US008680291B2

(12) United States Patent
Jung et al.

(10) Patent No.: US 8,680,291 B2
(45) Date of Patent: Mar. 25, 2014

(54) DIARYLHYDANTOIN COMPOUNDS

(75) Inventors: Michael E. Jung, Los Angeles, CA (US); Dongwon Yoo, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 544 days.

(21) Appl. No.: 12/257,743

(22) Filed: Oct. 24, 2008

(65) Prior Publication Data

US 2009/0111864 A1    Apr. 30, 2009

Related U.S. Application Data

(60) Provisional application No. 60/996,076, filed on Oct. 26, 2007.

(51) Int. Cl.
*A61K 31/4166* (2006.01)
*C07D 233/86* (2006.01)
*C07D 487/20* (2006.01)

(52) U.S. Cl.
USPC ............... 548/301.4; 548/316.7; 514/391

(58) Field of Classification Search
USPC ............................. 548/301.4, 316.7
See application file for complete search history.

(56) References Cited

U.S. PATENT DOCUMENTS

| | | |
|---|---|---|
| 3,823,240 A | 7/1974 | Sauli |
| 3,923,994 A | 12/1975 | Magnani |
| 3,984,430 A | 10/1976 | Curran |
| 4,097,578 A | 6/1978 | Perronnet et al. |
| 4,234,736 A | 11/1980 | Bernauer et al. |
| 4,304,782 A | 12/1981 | Dumont et al. |
| 4,312,881 A | 1/1982 | Wootton |
| 4,399,216 A | 8/1983 | Axel et al. |
| 4,407,814 A | 10/1983 | Bernauer et al. |
| 4,427,438 A | 1/1984 | Nagano et al. |
| 4,473,393 A | 9/1984 | Nagpal |
| 4,482,739 A | 11/1984 | Bernauer et al. |
| 4,559,157 A | 12/1985 | Smith et al. |
| 4,608,392 A | 8/1986 | Jacquet et al. |
| 4,636,505 A | 1/1987 | Tucker |
| 4,749,403 A | 6/1988 | Liebl et al. |
| 4,753,957 A | 6/1988 | Chan |
| 4,820,508 A | 4/1989 | Wortzman |
| 4,859,228 A | 8/1989 | Prisbylla |
| 4,873,256 A | 10/1989 | Coussediere et al. |
| 4,938,949 A | 7/1990 | Borch et al. |
| 4,944,791 A | 7/1990 | Schröder et al. |
| 4,992,478 A | 2/1991 | Geria |
| 5,010,182 A | 4/1991 | Brake et al. |
| 5,069,711 A | 12/1991 | Fischer et al. |
| 5,071,773 A | 12/1991 | Evans et al. |
| 5,084,472 A | 1/1992 | Moguilewsky et al. |
| 5,166,358 A | 11/1992 | Seuron et al. |
| 5,411,981 A | 5/1995 | Gaillard-Kelly et al. |
| 5,434,176 A | 7/1995 | Claussner et al. |
| 5,554,607 A | 9/1996 | Elokdah et al. |
| 5,556,983 A | 9/1996 | Claussner et al. |
| 5,589,497 A | 12/1996 | Claussner et al. |
| 5,614,620 A | 3/1997 | Liao et al. |
| 5,627,201 A | 5/1997 | Gaillard-Kelly et al. |
| 5,646,172 A | 7/1997 | Claussner et al. |
| 5,656,651 A | 8/1997 | Sovak et al. |
| 5,705,654 A | 1/1998 | Claussner et al. |
| 5,726,061 A | 3/1998 | Robbins et al. |
| 5,750,553 A | 5/1998 | Claussner et al. |
| 5,783,707 A | 7/1998 | Elokdah et al. |
| RE35,956 E | 11/1998 | Gaillard-Kelly et al. |
| 5,958,936 A | 9/1999 | Claussner et al. |
| 5,985,868 A | 11/1999 | Gray |
| 6,087,509 A | 7/2000 | Claussner et al. |
| 6,107,488 A | 8/2000 | Bouchet et al. |
| 6,172,076 B1 | 1/2001 | Embrey et al. |
| 6,235,910 B1 | 5/2001 | Beller et al. |
| 6,242,611 B1 | 6/2001 | Claussner et al. |
| 6,307,030 B1 | 10/2001 | French et al. |
| 6,350,763 B1 | 2/2002 | Kelly et al. |
| 6,472,415 B1 | 10/2002 | Sovak et al. |
| 6,479,063 B2 | 11/2002 | Weisman et al. |
| 6,489,163 B1 | 12/2002 | Roy et al. |
| 6,506,607 B1 | 1/2003 | Shyjan |
| 6,518,257 B1 | 2/2003 | Tasaka et al. |
| 6,828,471 B2 | 12/2004 | Sawyers et al. |
| 6,949,521 B2 | 9/2005 | Chu et al. |
| 7,138,421 B2 | 11/2006 | Cleve et al. |
| 7,271,188 B2 | 9/2007 | Tachibana et al. |

(Continued)

FOREIGN PATENT DOCUMENTS

| | | |
|---|---|---|
| AU | 217893 | 6/1958 |
| CN | 101032483 A | 9/2007 |

(Continued)

OTHER PUBLICATIONS

Wallen et al., "Androgen Receptor Gene Mutations in Hormone-Refractory Prostate Cancer", J. Pathology 1999, vol. 189, pp. 559-563.
Lu et al. "Molecular Mechanisms of Androgen-Independent Growth of Human Prostate Cancer LNCaP-Al Cells", Endocrinology 1999, vol. 140, No. 11, pp. 5054-5059.
Karp et al., Cancer Res. 56: 5547-5556., 1996.
Ausubel et al., Current Protocols in Molecular Biology, Wiley Interscience Publishers, (1995).
Sambrook et al., Molecular Cloning: A Laboratory Manual $2^{nd}$ edition (1989) Cold Spring Harbor Laboratory Press, Cold Spring Harbor, N.Y.
Chang et al., Science 240 (4850), 324-326 (1988).
NM_000044<http://www.ncbi.nlm.nih.gov:80/entrez/viewer.fcgi?cmd=Retrieve&db=nucleotide&list_uids=21322251&dopt=GenBank&term=sapiens+AR+androgen+receptor+prostate+cancer&qty=1>gi:21322251, printed Oct. 24, 2007.
*Mammalian Cell Biotechnology: a Practical Approach*, M. Butler, ed. (IRL Press, 1991).

(Continued)

*Primary Examiner* — Laura L. Stockton
(74) *Attorney, Agent, or Firm* — Venable LLP; Michael A. Gollin; Lars H. Genieser

(57) ABSTRACT

The present invention relates to diarylhydantoin compounds and methods for synthesizing them and using them in the treatment of hormone refractory prostate cancer.

12 Claims, No Drawings

(56) References Cited

U.S. PATENT DOCUMENTS

| | | |
|---|---|---|
| 7,601,748 B2 | 10/2009 | Cleve et al. |
| 7,709,517 B2 | 5/2010 | Sawyers et al. |
| 7,718,684 B2 | 5/2010 | Jung et al. |
| 8,110,594 B2 | 2/2012 | Jung et al. |
| 8,183,274 B2 | 5/2012 | Sawyers et al. |
| 2002/0133833 A1 | 9/2002 | Sawyers et al. |
| 2003/0225138 A1 | 12/2003 | Sircar et al. |
| 2004/0009969 A1 | 1/2004 | Cleve et al. |
| 2004/0116417 A1 | 6/2004 | Boubia et al. |
| 2005/0153968 A1 | 7/2005 | Bi et al. |
| 2006/0127902 A1 | 6/2006 | Madden et al. |
| 2007/0004753 A1 | 1/2007 | Sawyers et al. |
| 2007/0166717 A1 | 7/2007 | Sawyers et al. |
| 2007/0249697 A1 | 10/2007 | Tachibana et al. |
| 2007/0254933 A1* | 11/2007 | Jung et al. ............... 514/387 |
| 2008/0139634 A2 | 6/2008 | Jung et al. |
| 2009/0111864 A1 | 4/2009 | Jung et al. |
| 2010/0172975 A1 | 7/2010 | Sawyers et al. |
| 2010/0210665 A1 | 8/2010 | Sawyers et al. |
| 2011/0003839 A1 | 1/2011 | Jung et al. |

FOREIGN PATENT DOCUMENTS

| | | |
|---|---|---|
| DE | 2102605 | 7/1971 |
| DE | 2126187 | 12/1971 |
| DE | 2614831 A1 | 10/1977 |
| EP | 0 001 813 A1 | 5/1979 |
| EP | 0017976 A2 | 10/1980 |
| EP | 0017976 A3 | 10/1980 |
| EP | 0017976 A3 | 4/1981 |
| EP | 0017976 B1 | 6/1983 |
| EP | 0 091 596 A2 | 10/1983 |
| EP | 0 002 259 B1 | 10/1984 |
| EP | 0 091 596 A3 | 11/1984 |
| EP | 0144098 A1 | 6/1985 |
| EP | 0331232 A2 | 9/1989 |
| EP | 362179 | 4/1990 |
| EP | 0 436 426 A1 | 7/1991 |
| EP | 0 494 819 A1 | 1/1992 |
| EP | 0 578 516 A1 | 5/1993 |
| EP | 0 580 459 A1 | 5/1993 |
| EP | 0572191 A1 | 12/1993 |
| EP | 0 580 459 B1 | 1/1994 |
| EP | 0 494 819 B1 | 7/1996 |
| EP | 0770613 A1 | 5/1997 |
| EP | 0 721 944 B1 | 1/2001 |
| EP | 1 790 640 A | 5/2007 |
| EP | 2400847 | 1/2012 |
| FR | 2 075 751 | 10/1971 |
| FR | 2 329 276 | 5/1977 |
| FR | 2 693 461 A1 | 1/1994 |
| FR | 2 715 402 A1 | 1/1994 |
| FR | 2 845 384 A1 | 10/2002 |
| JP | 48 87030 | 11/1973 |
| JP | 59210083 | 11/1984 |
| JP | 1009978 A | 1/1989 |
| JP | 2019363 A | 1/1990 |
| JP | 6-073017 A | 3/1994 |
| JP | 10-510845 A | 10/1998 |
| JP | 38 45455 B2 | 11/2006 |
| JP | 2009-531449 A | 9/2009 |
| WO | WO 90/13646 | 11/1990 |
| WO | WO 95/18794 A1 | 7/1995 |
| WO | WO 97/00071 | 1/1997 |
| WO | WO 97/19064 | 5/1997 |
| WO | WO 97/19931 | 6/1997 |
| WO | WO 00/17163 | 3/2000 |
| WO | WO 00/26195 A1 | 5/2000 |
| WO | WO 00/44731 A1 | 8/2000 |
| WO | WO 01/07048 A1 | 2/2001 |
| WO | WO 01/92253 A2 | 12/2001 |
| WO | WO-01/94346 A1 | 12/2001 |
| WO | WO 02/053155 A1 | 7/2002 |
| WO | WO 02/081453 A1 | 10/2002 |
| WO | WO 03/029245 A1 | 4/2003 |
| WO | WO 03/032994 A2 | 4/2003 |
| WO | WO 03/057220 A1 | 7/2003 |
| WO | WO 03/093243 A1 | 11/2003 |
| WO | WO 03/096980 | 11/2003 |
| WO | WO 2004/022572 A1 | 3/2004 |
| WO | WO 2004/031160 A2 | 4/2004 |
| WO | WO 2004/070050 A2 | 8/2004 |
| WO | WO 2004/111031 A1 | 12/2004 |
| WO | WO 2005/042488 A1 | 5/2005 |
| WO | WO 2005/059109 | 6/2005 |
| WO | WO2005/059109 A3 | 6/2005 |
| WO | WO 2005/060661 | 7/2005 |
| WO | WO 2005/089752 | 9/2005 |
| WO | WO-2005/089752 A2 | 9/2005 |
| WO | WO 2005/099693 | 10/2005 |
| WO | WO 2006/010642 | 2/2006 |
| WO | WO-2006/010642 A1 | 2/2006 |
| WO | WO 2006/028226 A | 3/2006 |
| WO | WO-2005/059109 A3 | 8/2006 |
| WO | WO 2006/124118 A1 | 11/2006 |
| WO | WO-2006124118 A1 * | 11/2006 |
| WO | WO 2007/045877 A1 | 4/2007 |
| WO | WO 2007/126765 | 11/2007 |
| WO | WO 2007/127010 | 11/2007 |
| WO | WO 2008/119015 A2 | 10/2008 |
| WO | WO-2009/055053 A2 | 4/2009 |
| WO | WO-2009/076408 A2 | 6/2009 |
| WO | WO-2010/099238 A1 | 9/2010 |

OTHER PUBLICATIONS

Graham and van der Eb, *Virology*, 52:456-467., 1973.
Keown et al., *Methods in Enzymology*, 185:527-537 (1990).
Mansour et al., *Nature*, 336:348-352 (1988).
Muller et al., 1991, Mol. & Cell. Bio. 11:1785.
Urlaub et al., *Proc. Natl. Acad. Sci. USA*, 77:4216 (1980).
Stinchcomb et al., *Nature*, 282:39 (1979).
Kingsman et al., *Gene*, 7: 141 (1979).
Tschumper et al., *Gene*, 10: 157 (1980).
Jones, *Genetics*, 85:12 1977., pp. 23-33.
Feldman, B.J. & Feldman, D. The development of androgen-independent prostate cancer. Nat Rev Cancer 1, 34-45 (2001).
Gelmann, E.P. Molecular biology of the androgen receptor. J Clin Oncol 20, 3001-15 (2002).
Balk, S.P. Androgen receptor as a target in androgen-independent prostate cancer. Urology 60, 132-8; discussion 138-9 (2002).
Taplin, M.E. et al. Selection for androgen receptor mutations in prostate cancers treated with androgen antagonist. Cancer Res 59, 2511-5 (1999).
Taplin, M.E. et al. Androgen receptor mutations in androgen-independent prostate cancer: Cancer and Leukemia Group B Study 9663. J Clin Oncol 21, 2673-8 (2003).
Visakorpi, T. et al. In vivo amplification of the androgen receptor gene and progression of human prostate cancer. Nat Genet 9, 401-6 (1995).
Taplin, M.E. et al. Mutation of the androgen-receptor gene in metastatic androgen-independent prostate cancer. N Engl J Med 332, 1393-8 (1995).
Veldscholte, J. et al. A mutation in the ligand binding domain of the androgen receptor of human LNCaP cells affects steroid binding characteristics and response to anti-androgens. Biochem Biophys Res Commun 173, 534-40 (1990).
Matias, P.M. et al. Structural basis for the glucocorticoid response in a mutant human androgen receptor (AR(ccr)) derived from an androgen-independent prostate cancer. J Med Chem 45, 1439-46 (2002).
Craft, N., Shostak, Y., Carey, M. & Sawyers, C.L. A mechanism for hormone-independent prostate cancer through modulation of androgen receptor signaling by the HER-2/neu tyrosine kinase. Nat Med 5, 280-5 (1999).
Gioeli, D. et al. Androgen receptor phosphorylation. Regulation and identification of the phosphorylation sites. J Biol Chem 277, 29304-14 (2002).
Kato, S. et al. Activation of the estrogen receptor through phosphorylation by mitogen-activated protein kinase. Science 270, 1491-4 (1995).

(56) References Cited

OTHER PUBLICATIONS

Font de Mora, J. & Brown, M. AIB1 is a conduit for kinase-mediated growth factor signaling to the estrogen receptor. Mol Cell Biol 20, 5041-7 (2000).
Tremblay, A., Tremblay, G.B., Labrie, F. & Giguere, V. Ligand-independent recruitment of SRC-1 to estrogen receptor beta through phosphorylation of activation function AF-1. Mol Cell 3, 513-9 (1999).
Gregory, C.W. et al. A mechanism for androgen receptor-mediated prostate cancer recurrence after androgen deprivation therapy. Cancer Res 61, 4315-9 (2001).
Li, P. et al. Heterogeneous expression and functions of androgen receptor co-factors in primary prostate cancer. Am J Pathol 161, 1467-74 (2002).
Glass, C.K. & Rosenfeld, M.G. The coregulator exchange in transcriptional functions of nuclear receptors. Genes Dev 14, 121-41 (2000).
Raffo, A.J. et al. Overexpression of bcl-2 protects prostate cancer cells from apoptosis in vitro and confers resistance to androgen depletion in vivo. Cancer Res 55, 4438-45 (1995).
McDonnell, T.J. et al. Expression of the protooncogene bcl-2 in the prostate and its association with emergence of androgen-independent prostate cancer. Cancer Res 52, 6940-4 (1992).
Kinoshita, H. et al. Methylation of the androgen receptor minimal promoter silences transcription in human prostate cancer. Cancer Res 60, 3623-30 (2000).
Shang, Y., Myers, M. & Brown, M. Formation of the androgen receptor transcription complex. Mol Cell 9, 601-10 (2002).
Zhau, H.Y. et al. Androgen-repressed phenotype in human prostate cancer. Proc Natl Acad Sci U S A 93,15152-7 (1996).
Wainstein, M.A. et al. CWR22: androgen-dependent xenograft model derived from a primary human prostatic carcinoma. Cancer Res 54, 6049-52 (1994).
Ellis, W.J. et al. Characterization of a novel androgen-sensitive, prostate-specific antigen-producing prostatic carcinoma xenograft: LuCaP 23. Clin Cancer Res 2, 1039-48 (1996).
Horoszewicz, J.S. et al. LNCaP model of human prostatic carcinoma. Cancer Res 43, 1809-18 (1983).
Klein, K.A. et al. Progression of metastatic human prostate cancer to androgen independence in immunodeficient SCID mice. Nat Med 3, 402-8 (1997).
Perou, C.M. et al. Molecular portraits of human breast tumors. Nature 406, 747-52 (2000).
Gregory, C.W., Johnson, R.T., Jr., Mohler, J.L., French, F.S. & Wilson, E.M. Androgen receptor stabilization in recurrent prostate cancer is associated with hypersensitivity to low androgen. Cancer Res 61, 2892-8. (2001).
Huang, Z.Q., Li, J. & Wong, J. AR possess an intrinsic hormone-independent transcriptional activity. Mol Endocrinol 16, 924-37 (2002).
Matias, P.M. et al. Structural evidence for ligand specificity in the binding domain of the human androgen receptor. Implications for pathogenic gene mutations. J Biol Chem 275, 26164-71 (2000).
Lobaccaro, J.M. et al. Molecular modeling and in vitro investigations of the human androgen receptor DNA-binding domain: application for the study of two mutations. Mol Cell Endocrinol 116, 137-47 (1996).
Migliaccio, A. et al. Steroid-induced androgen receptor-oestradiol receptor beta-Src complex triggers prostate cancer cell proliferation. Embo J 19, 5406-17 (2000).
Kousteni, S. et al. Nongenotropic, sex-nonspecific signaling through the estrogen or androgen receptors: dissociation from transcriptional activity. Cell 104, 719-30 (2001).
Manolagas, S.C., Kousteni, S. & Jilka, R.L. Sex steroids and bone. Recent Prog Horm Res 57, 385-409 (2002).
DePrimo, S.E. et al. Transcriptional programs activated by exposure of human prostate cancer cells to androgen. Genome Biol 3, RESEARCH0032 (2002).
Masiello, D., Cheng, S., Bubley, G.J., Lu, M.L. & Balk, S.P. Bicalutamide functions as an androgen receptor antagonist by assembly of a transcriptionally inactive receptor. J Biol Chem 277, 26321-6 (2002).
Edwards, J., Krishna, N.S., Grigor, K.M. & Bartlett, J.M. Androgen receptor gene amplification and protein expression in hormone refractory prostate cancer. Br J Cancer 89, 552-6 (2003).
Laitinen, S., Karhu, R., Sawyers, C.L., Vessella, R.L. & Visakorpi, T. Chromosomal aberrations in prostate cancer xenografts detected by comparative genomic hybridization. Genes Chromosomes Cancer 35, 66-73 (2002).
Grad, J.M., Dai, J.L., Wu, S. & Burnstein, K.L. Multiple androgen response elements and a Myc consensus site in the androgen receptor (AR) coding region are involved in androgen-mediated up-regulation of AR messenger RNA. Mol Endocrinol 13, 1896-911 (1999).
Craft, N. et al. Evidence for clonal outgrowth of androgen-independent prostate cancer cells from androgen-dependent tumors through a two-step process. Cancer Res 59,5030-6 (1999).
Ellwood-Yen, K. et al. Myc-driven murine prostate cancer shares molecular features with human prostate tumors. Cancer Cell 4, 223-38 (2003).
Wang, S. et al. Prostate-specific deletion of the murine Pten tumor suppressor gene leads to metastatic prostate cancer. Cancer Cell 4, 209-21 (2003).
Shiau, A.K. et al. The structural basis of estrogen receptor/coactivator recognition and the antagonism of this interaction by tamoxifen. Cell 95, 927-37 (1998).
Norris, J.D. et al. Peptide antagonists of the human estrogen receptor. Science 285, 744-6 (1999).
Baek, S.H. et al. Exchange of N-CoR corepressor and Tip60 coactivator complexes links gene expression by NF-kappaB and beta-amyloid precursor protein. Cell 110, 55-67 (2002).
Shang, Y. & Brown, M. Molecular determinants for the tissue specificity of SERMs. Science 295, 2465-8 (2002).
Schellhammer, P.F. et al. Prostate specific antigen decreases after withdrawal of antiandrogen therapy with bicalutamide or flutamide in patients receiving combined androgen blockade. J Urol 157, 1731-5 (1997).
Sack, J.S. et al. Crystallographic structures of the ligand-binding domains of the androgen receptor and its T877A mutant complexed with the natural agonist dihydrotestosterone. Proc Natl Acad Sci U S A 98, 4904-9 (2001).
Zhou, Z.X., Sar, M., Simental, J.A., Lane, M.V. & Wilson, E.M. A ligand-dependent bipartite nuclear targeting signal in the human androgen receptor. Requirement for the DNA-binding domain and modulation by NH2-terminal and carboxyl-terminal sequences. J Biol Chem 269, 13115-23 (1994).
Chen, C.D., Welsbie, D.S., Tran, C., Baek, S.H., Chen, R., Vessella, R., Rosenfeld, M.G., and Sawyers, C.L., Molecular determinants of resistance to antiandrogen therapy, Nat. Med., 10: 33-39, 2004.
*The Pharmacological Basis of Therapeutics*, Goodman and Gilman, eds., Macmillan Publishing Co., New York., 2001, Table of Contents only.
The Practice of Medicinal Chemistry, Camille G. Wermuth et al., Ch 31, (Academic Press, 1996).
Design of Prodrugs, edited by H. Bundgaard, (Elsevier, 1985)., Table of Contents Only.
A Textbook of Drug Design and Development, P. Krogsgaard-Larson and H. Bundgaard, eds. Ch 5, pp. 113-191 (Harwood Academic Publishers, 1991).
Remington: The Science and Practice of Pharmacy, 19th Edition, Gennaro (ed.) 1995, Mack Publishing Company, Easton, PA, Table of Contents Only.
Teutsch, G.; Goubet, F.; Battmann, T.; Bonfils, A.; Bouchoux, F.; Cerede, E.; Gofflo, D.; Gaillard-Kelly, M.; Philibert. D. ..*J. Steroid Biochem. Molec. Biol*. 1994, 48, 111-119.
Van Dort, M. E.; Robins, D. M.; Wayburn, B. *J. Med. Chem*. 2000, 43, 3344-3347.
Homma,S., et al., "Differential levels of human leukocyte antigen-class I, multidrug-resistance 1 and androgen receptor expressions in untreated prostate cancer cells: the robustness of prostate cancer", Oncol. Rep. 18 (2), 343-346 (2007).

(56) References Cited

OTHER PUBLICATIONS

Cai,C., et al., "c-Jun has multiple enhancing activities in the novel cross talk between the androgen receptor and Ets variant gene 1 in prostate cancer", Mol. Cancer Res. 5(7), 725-735 (2007).
Su,Q.R., et al., "Polymorphisms of androgen receptor gene in childhood and adolescent males with first-onset major depressive disorder and associationwith related symptomatology", Int. J. Neurosci. 117 (7), 903-917 (2007).
Brockschmidt,F.F., et al., "The two most common alleles of the coding GGN repeat in the androgen receptor gene cause differences in protein function", J. Mol. Endocrinol. 39 (1), 1-8 (2007).
Hamilton-Reeves,J.M., et al, "Isoflavone-rich soy protein isolate suppresses androgen receptor expression without altering estrogen receptor-beta expression or serum hormonal profiles in men at high risk of prostate cancer", J. Nutr. 137 (7), 1769-1775 (2007).
Sweet,C.R., et al., "A unique point mutation in the androgen receptor gene in a family with complete androgen insensitivity syndrome", Fertil. Steril. 58 (4), 703-707 (1992).
Batch,J.A., et al., "Androgen receptor gene mutations identified by SSCP in fourteen subjects with androgen insensitivity syndrome", Hum. Mol. Genet. 1 (7), 497-503 (1992).
Wooster,R., et al., "A germline mutation in the androgen receptor gene in two brothers with breast cancer and Reifenstein syndrome", Nat. Genet. 2 (2), 132-134 (1992).
Saunders,P.T., et al., "Point mutations detected in the androgen receptor gene of three men with partial androgen insensitivity syndrome", Clin. Endocrinol. (Oxf) 37 (3), 214-220 (1992).
Zoppi,S., et al. "Amino acid substitutions in the DNA-binding domain of the human androgen receptor are a frequent cause of receptor-binding positive androgen resistance", Mol. Endocrinol. 6 (3), 409-415 (1992).
International Search Report issued in PCT Application PCT/US2005/005529, mailed on Nov. 10, 2005.
International Search Report issued in PCT Application PCT/US2004/042221, mailed on Jun. 20, 2005.
Wang, Long G., et al., "Overexpressed androgen receptor linked to p21WAF1 silencing may be responsible for androgen independence and resistance to apoptosis of a prostate cancer cell line", Cancer Research 61 (20), pp. 7544-7551 (Oct. 15, 2001).
Shi, Xu-Bao, et al., "Functional analysis of 44 mutant androgen receptors from human prostate cancer", Cancer Research 62 (5), pp. 1496-1502 (Mar. 1, 2002).
Navone, N. M., et al., "Model Systems of Prostate Cancer: Uses and Limitations" Cancer Metastasis, Kluwer Academic Publishers, Dordrecht, NL, 17 (4), 1999, pp. 361-371.
Extended European Search Report issued in European Patent Application No. EP 06748863.5, mailed on Feb. 12, 2009.
S.Ouk et al., "Development of Androgen Receptor Inhibitors for Hormone-refractory Prostate Cancer", Prostate Cancer Foundation Meeting, Scottsdale, AZ, Sep. 29-Oct. 1, 2005.
Cousty-Berlin, et al., "Preliminary Pharmacokinetics and Metabolism of Novel Non-steroidal Antiandrogens in the Rat: Relation of their Systemic Activity to the Formation of a Common Metabolite," J. Steroid Biochem. Molec. Biol., vol. 51, No. 1/2, pp. 47-55 (1994).
Feher, et al., "BHB: A Simple Knowledge-Based Scoring Function to Improve the Efficiency of Database Screening," J. Chem. Inf. Comput. Sci., vol. 43, pp. 1316-1327 (2003).
Foury, et al., "Control of the Proliferation of Prostate Cancer Cells by an Androgen and Two Antiandrogens. Cell Specific Sets of Responses," J. Steroid Biochem. Molec. Biol., vol. 66, No. 4, pp. 235-240 (1998).
Goubet, et al., Conversion of a Thiohydantoin to he Corresponding Hydantoin via a Ring-Opening/Ring Closure Mechanism, Tetrahedron Letters, vol. 37, No. 43, pp. 7727-7730 (1996).
Karvonen, et al., "Interaction of Androgen Receptors with Androgen Response Element in Intact Cells," The Journal of Biological Chemistry, vol. 272, No. 25, pp. 15973-15979 (1997).
Kemppainen, et al., "Distinguishing Androgen Receptor Agonists and Antagonists: Distinct Mechanisms of Activation by Medroxyprogesterone Acetate and Dihydrotestosterone," Mol. Endocrinol., vol. 13, pp. 440-454 (1999); mend.endojournals.org.
Marhefka, et al., "Homology Modeling Using Multiple Molecular Dynamics Simulations and Docking Sudies of the Human Androgen Receptor Ligand Binding Domain Bound to Testosterone and Nonsteroidal Ligands," J. Med. Chem., vol. 44, No. 11, pp. 1729-1740 (2001).
Matias, et al., "Local Inhibition of Sebaceous Gland Growth by Topically Applied RU 58841,"NY Acad. Sci., vol. 761, pp. 56-65 (1995).
Sderholm, et al., "Three-Dimensional Structure—Activity Relationships of Nonsteroidal Ligands in Complex with Androgen Receptor Ligand-Binding Domain," J. Med. Chem., vol. 48, No. 4, pp. 917-925 (2005).
Sperry, et al., Androgen binding profiles of two distinct nuclear androgen receptors in Atlantic croaker (Micropogonias undulates), Journal of Steroid Biochemistry & Molecular Biology, vol. 73, pp. 93-103 (2000).
Zarghami, et al., "Steroid hormone regulation of prostate-specific antigen gene expression in breast cancer," British Journal of Cancer, vol. 75, No. 4, pp. 579-588 (1997).
International Search Report issued in PCT Application PCT/US2007/07485, mailed on Sep. 4, 2008.
Written Opinion issued in PCT Application PCT/US2007/07485, mailed on Sep. 4, 2008.
International Search Report issued in International Application No. PCT/US2008/012149 mailed on Apr. 29, 2009.
Written Opinion issued in International Application No. PCT/US2008/012149, mailed on Apr. 29, 2009.
Office Action issued in U.S. Appl. No. 10/590,445, mailed on Mar. 2, 2009.
International Search Report issued in International Application No. PCT/US2007/007854, mailed on Apr. 15, 2008.
Written Opinion issued in International Application No. PCT/US2007/007854, mailed on Apr. 15, 2008.
International Search Report issued in PCT Application No. PCT/US2004/042221, mailed on Jun. 20, 2005.
Written Opinion issued in PCT Application No. PCT/US2004/042221, mailed on Jun. 20, 2005.
Written Opinion issued in PCT Application No. PCT/US2005/005529, mailed on Nov. 10, 2005.
Written Opinion issued in PCT Application No. PCT/US2006/011417, mailed on Jul. 3, 2006.
Data Sheet from U.S. Patent and Trademark Office (USPTO) U.S. Appl. No. 08/807,760, 1998.
Notice of References Cited from U.S. Patent and Trademark Office (USPTO) U.S. Appl. No. 08/807,760.
Office Action of Jan. 18, 1994 from U.S. Patent and Trademark Office for U.S. Appl. No. 08/064,257.
Office Action (paper No. 7) from U.S. Patent and Trademark Office for U.S. Appl. No. 08/064,257, 1994.
Office Action (paper No. 10) from U.S. Patent and Trademark Office for U.S. Appl. No. 08/064,257, 1994.
Office Action of Aug. 14, 1992 from U.S. Patent and Trademark Office for U.S. Appl. No. 07/819,110.
Notice of References Cited of Jul. 24, 1992 from U.S. Patent and Trademark Office for U.S. Appl. No. 07/819,110.
Office Action of Feb. 22, 1993 from U.S. Patent and Trademark Office for U.S. Appl. No. 07/819,110.
Office Action of Sep. 2, 1993 from U.S. Patent and Trademark Office for U.S. Appl. No. 07/819,110.
Office Action of Jun. 1, 1994 from U.S. Patent and Trademark Office for U.S. Appl. No. 07/819,110.
M.J. Linja et al., "Amplification and overexpression of androgen receptor gene in hormone-refractory prostate cancer", Cancer Research, vol. 61 (May 1, 2001) pp. 3550-3555.
J. Holzbeierlein et al., "Gene Expression Analysis of Human Prostate Carcinoma during Hormonal Therapy Identifies Androgen-Responsive Genes and Mechanisms of Therapy Resistance", Am. J. Pathology, vol. 164, No. 1 (Jan. 2004) pp. 217-227.
C.D. Chen et al., "Molecular determinants of resistance to antiandrogen therapy", Nature Medicine, vol. 10, No. 1 (Jan. 2004) pp. 33-39.

(56) References Cited

OTHER PUBLICATIONS

Office Action of Jul. 23, 2008 from U.S. Patent and Trademark Office for U.S. Appl. No. 10/590,445.
Karp et al., "Prostate Cancer Prevention: Investigational Approaches and Opportunities", Cancer Res., v. 56 (Dec. 15, 1996) pp. 5547-5556.
Graham and van der Eb, "A new technique for the assay of infectivity of human adenovirus 5 DNA", Virology, v. 52(2) (Apr. 1973) pp. 456-467.
P.J. Creaven et al., "Pharmacokinetics and Metabolism of Nilutamide", Supp. Urology, vol. 37, No. 2 (Feb. 1991) pp. 13-19.
Singh et al., "Androgen Receptor Antagonists (Antiandrogens): Structure-Activity Relationships", Current Medicinal Chemistry, 2000, 7, pp. 211-247.
Bohl et al., "Structural basis for antagonism and resistance of bicalutamide in prostate cancer", Proc. Nat. Acad. Sci., 2005, v. 102(17), pp. 6201-6206.
Nam et al., "Action of the Src Family Kinase Inhibitor, Dasatinib (BMS-354825), on Human Prostate Cancer Cells", Cancer Res., 2005, v. 65(20), pp. 9185-9189.
Burnstein et al. Androgen Glucocorticoid Regulation of Androgen Receptor cDNA Expression. Molecular and Cellular Endocrinology. 1995. v. 115, pp. 177-186.
Cinar et al. Androgen Receptor Mediates the Reduced Tumor Growth, Enhanced Androgen Responsiveness, and Selected Target Gene Transactivation in Human Prostate Cancer Cell Line. Cancer Research. 2001. v. 61. pp. 7310-7317.
Szelei et al. Androgen-Induced Inhibition of Proliferation in Human Breast Cancer MCF7 Cells Transfected with Androgen Receptor. Endocrinology. 1997. v. 138 (4). pp. 1406-1412.
Raffo et al. Overexpression of bcl-2 Protects Prostate Cancer Cells from Apoptosis in Vitro and Confers Resistance to Androgen Depletion in Vivo. Cencer Research. 1995. v. 55. 4438-4445.
Office Action of Aug. 11, 2009 from U.S. Patent and Trademark Office for U.S. Appl. No. 10/583,280.
A.M. Soto et al., "Control of Cell Proliferation: Evidence for Negative Control on Estrogen-sensitive T47D Human Breast Cancer Cells", Cancer Research, 46, (1986), pp. 2271-2275.
Presentation of Charles Sawyers, Prostate Cancer Foundation Scientific Retreat, Scottsdale, Arizona, Sep. 29-Oct. 1, 2005.
Abstract submitted by Samedy Ouk, Prostate Cancer Foundation Scientific Retreat, Scottsdale, Arizona, Sep. 29-Oct. 1, 2005.
Office Action mailed Oct. 8, 2010 in U.S. Appl. No. 11/730,168.
Office Action mailed Oct. 1, 2010 in U.S. Appl. No. 12/708,523.
Scher et al., Antitumour activity of MDV3100 in castration-resistant prostate cancer: a phase 1-2 study. 2010. Lancet. 375:1437-1446.
Jung et al., Structure—Activity Relationship for Thiohydantoin Androgen Receptor Antagonists for Castration-Resistant Prostate Cancer (CRPC). 2010. J Med Chem. 53:2779-2796.
Schafer et al., Failure is an Option: ; learning from Unsuccessful Proof-of-Concept trials. 2008. Drug Discovery Today. 13:913-916.
Hörig et al., From bench to clinic and back: Perspective on 1$^{st}$ IQPC Translational Research Conference. 2004. Journal of Translational Medicine. 2:44.
Elokdah Hassan et al., Design, synthesis, and biological evaluation of thio-containing compounds with serum HDL-cholesterol-elevating properties. J Med Chem. 47(29): 681-695, 2004.
Database CA Chemical Abstracts Service, Columbus, Ohio, US; Jan. 1, 1994. Dhal, P. N. et al. Synthesis of thiohydantoins, thiazolidones, and their derivatives from N1-(4'-arylthiazol-2'-yl)thioureas. J Ind Chem Soc. 50:680-684. 1973.
Supplementary European Search in EP 07754060 mailed on Oct. 11, 2010.
Nakajima et al., Activated Dimethyl sulfoxide dehydration of amide and its application to one-pot preparation of benzyl-type prefluoroimidates. 2002. Tetrahedron. 58:3561-3577.
Examiner Search Results Associated with Office Action mailed Oct. 8, 2010 in U.S. Appl. No. 11/730,168.
Notice of Allowance from the U.S. Patent Office issued in U.S. Appl. No. 13/333,543 dated Mar. 19, 2013.

Office Action from the U.S. Patent Office issued in U.S. Appl. No. 13/448,964 dated Feb. 28, 2013.
Park K. et al., "Metabolism of Fluorine-Containing Drugs," Annu. Rev. Pharmacol. Toxicol. 2001, vol. 41, pp. 443-470.
Statement by Applicant of Mar. 21, 2013 (incorporated into filed IDS Transmittal Letter).
U.S. Appl. No. 60/680,835, filed May 13, 2005, Sawyers et al.
U.S. Appl. No. 60/750,351, filed Dec. 15, 2005, Jung et al.
U.S. Appl. No. 60/756,552, filed Jan. 6, 2006, Jung et al.
Database CA, Chemical Abstracts Service (1994), Summary of Dhal P.N., J Indian Chem Soc 50 (1973) 680-684.
International Search Report issued in PCT Application PCT/US96/10286 on Oct. 4, 1996.
Notice of Allowance issued in U.S. Appl. No. 11/730,168 dated Jun. 10, 2011.
Notice of Allowance issued in U.S. Appl. No. 10/583,280 dated Jun. 9, 2011.
Notice of Allowance issued in U.S. Appl. No. 11/433,829 dated Jun. 8, 2009.
Notice of Allowance issued in U.S. Appl. No. 11/433,829 dated Nov. 18, 2009.
Office Action issued in U.S. Appl. No. 10/583,280 mailed on Apr. 2, 2010.
Office Action issued in U.S. Appl. No. 11/433,829 mailed on Jan. 27, 2009.
Office Action issued in U.S. Appl. No. 12/257,743 dated Jun. 29, 2010.
Raynaud et al., 1979, Action of a non-steroid anti-androgen, RU 23908, in peripheral and central tissues, Journal of Steroid Biochemistry, 11: 93-99.
Restriction Requirement issued in U.S. Appl. No. 10/583,280 mailed on Aug. 11, 2009.
Restriction Requirement Issued in U.S. Appl. No. 10/590,445 mailed on Jun. 5, 2008.
Restriction Requirement Issued in U.S. Appl. No. 10/590,445 mailed on Mar. 26, 2008.
Restriction Requirement issued in U.S. Appl. No. 11/433,829 mailed on Nov. 3, 2008.
Restriction Requirement issued in U.S. Appl. No. 12/257,743 mailed on Jul. 6, 2009.
Supplementary European Search Report issued in EP 07754060 mailed on Oct. 11, 2010.
Espada et al., "$N_3$-Arylspiroimidazolidine-2,4-Diones, $N_3$-Arylspiroimidazolidine-2-Thio-4-ones and 4-Hydroxy Derivatives. Synthesis and Anthelminitic Activity," IL FARMACO, vol. 45, No. 11, pp. 1237-1243 & title page (1990).
Mancheva et al., "Preparation and Characterization of Diphenylindenonylthiohydantoin Derivatives of Non-Protein Cycloaliphatic Amino Acids," Dokladi na Bulgarskata Akademiya na Naukite (Comptes rendu de l'Academie bulgare des Sciences),vol. 45, No. 11, pp. 67-70 & title page (1992).
Ametamey et al., "Reaktionen von 3-(Dimethylamino)-2$H$-azirinen mit 1,3-Benzoxazol-2(3$H$)-thion," Helvetica Chima Acta, vol. 73, No. 3, pp. 599-607 & title page (1990).
Hough, "Synthesis of Imidazolin-2-ones by Rearrangement of $N$-Carbamoyliminium Salts Derived From 4-Hydroxyimidazolidin-2-ones," Journal of Heterocyclic Chemistry, vol. 26, No. 6, pp. 1523-1525 & title page (1989).
Günzl et al., "Zur Chemie der vicinalen Triketone, XIII, Versuche zur Darstellung von Schiffschen Basen aus cyclischen, vicinalen Triketonen," Monatshefte für Chemie, vol. 113, No. 11, pp. 1299-1310 & title page (1982).
Crooks et al., "The Structure of Some Reaction Products of 2,3-Dihydrophenalene-1,2,3-Trione with Urea and its Homologues," Gazzetta Chimica Italiana, vol. 107, No. 5-6, pp. 353-354 & title page (1977).
Dyer et al., "Preparation of Polyhydrouracils and Polyiminoimidazolidinones," Journal of Polymer Science, Part A-1, vol. 7, pp. 833-849 & title page (1969).
Umezawa et al., "The Synthesis of Cyclic α-Amino Acids," Bulletin of the Chemical Society of Japan, vol. 40, No. 1, pp. 209-214 & title page (1967).

(56) References Cited

OTHER PUBLICATIONS

Oldfield et al., "The Chemistry and Pharmacology of a Series of Cycloalkanespiro-5'-hydantoins," Journal of Medical Chemistry, vol. 8, No. 2, pp. 239-249 (1965).
Nicole et al., "Synthèses D'Acides Aminés Cycliques ÀPartir de Dérivés de L'Acide Adipique," Canadian Journal of Chemistry, vol. 40, pp. 353-366 (1962).
Chemical Abstracts, vol. 114, p. 185368 (May 13, 1991).
Krüger et al., "Synthese and Reaktionen von 1-(1-Cyanoalkyl)-1-hydroxyharnstoffen," Arch. Pharm. (Weinheim), vol. 311, pp. 39-47 (1978).
Dhal et al., "Synthesis of Thiohydantoins, Thiazolidones and Their Derivatives from N-(4'-Aryl Thiazole 2'-YL) Thioureas," J. Indian Chem. Soc., vol. L, pp. 680-684 (Oct. 1973).
Singh, "Amidine: Structure, Reactivity and Complexation Behaviour," Int'l J. of Chem. Tech. Res., vol. 1(2), pp. 250-264 (2009).
Aly et al., "Functionality of amidines and amidrazones," ARKIVOC (i), pp. 153-194 (2008).
Chemical Abstracts Search provided with Oct. 8, 2010 Office Action in U.S. Appl. No. 11/730,168.
Notice of Allowance issued in U.S. Appl. No. 11/730,168 mailed Sep. 20, 2011.
Corrected Notice of Allowability issued in U.S. Appl. No. 11/730,168 mailed Dec. 22, 2011.
Corrected Notice of Allowability issued in U.S. Appl. No. 11/730,168 mailed Jan. 19, 2012.
Rao et al., "Merits and Considerations in the Use of Anti-Androgen," J. Steroid Biochem. 31 (4B), pp. 731-737 (1988).
European Search Report dated Jul. 20, 2011 for European Application No. 07754060.7, 7 pages.
Extended European Search Report dated Aug. 8, 2011 (search completed Jul. 12, 2011) for European Application No. 11163948.0, 10 pages.
WO 2003/096980 A3 (International Search Report for PCT/US2003/015375), mailed Dec. 3, 2003.
Final Office Action dated May 5, 2011, issued in related U.S. Appl. No. 12/708,523.
Notice of Allowance dated Dec. 16, 2011, issued in related U.S. Appl. No. 12/708,523.
Second Notice of Allowance dated Mar. 26, 2012, issued in related U.S. Appl. No. 12/708,523.
Office Action dated Jun. 12, 2012, issued in U.S. Appl. No. 13/333,543.
Abrahamsson, P.A. et al., "Risks and Benefits of Hormonal Manipulation as Monotherapy or Adjuvant Treatment in Localised Prostate Cancer," European Urology, 48, pp. 900-905 (2005).
International Search Report issued in PCT Application No. PCT/US06/11417 dated Jul. 3, 2006.
Office Action in U.S. Appl. No. 10/583,280 mailed on Nov. 29, 2010.
Zajchowski et al. Estrogen inhibits the growth of estrogen receptor-negative, but not estrogen receptor-positive, human mammary epithelial cells expressing a recombinant estrogen receptor. 1993. Cancer Research. 53:5004-5011.
Notice of References cited from U.S. Patent and Trademark Office (USPTO) U.S. Appl. No. 08/807,760 (1997).
Office Action (paper No. 10) from U.S. Patent and Trademark Office (USPTO) for U.S. Appl. No. 08/064,257 (mailed Sep. 27, 1994).
Office Action (paper No. 7) from U.S. Patent and Trademark Office (USPTO) for U.S. Appl. No. 08/064,257 (mailed Aug. 31, 1994).
Notice of Allowance issued in U.S. Appl. No. 12/294,881 mailed Jun. 25, 2012.
Notice of Allowance issued in U.S. Appl. No. 12/708,531 mailed May 25, 2012.
Office Action issued in U.S. Appl. No. 12/708,531 mailed Nov. 14, 2011.
European Office Action issued in a European Application No. 11 178 889.9 dated Aug. 29, 2012.
Office Action from the US Patent and Trademark Office (USPTO) issued in U.S. Appl. No. 13/448,964 dated Sep. 18, 2012.
Patani et al., "Bioisiterism: A Rational Approach in Drug Design," Chem. Rev. 1996, vol. 96, pp. 3147-3176.
Clegg et al., "ARN-509: A Novel Antiandrogen for Prostate Cancer Treatment," *Cancer Res.* 2012; 72:1494-1503.
European Search Report issued in Application No. 12193684.3 dated Jan. 22, 2013.
Examination Report issued in New Zealand Application No. 601503 dated Jul. 31, 2012.
Examination Report issued in Australian Application No. 2007245022 dated Nov. 12, 2012.
Notice of Allowance issued in U.S. Appl. No. 13/448,964 dated May 31, 2013.
Notice of Allowability issued in U.S. Appl. No. 13/333,543 dated Jun. 20, 2013.
Paul et al., "Antiandrogen Withdrawal Syndrome Associated with Prostate Cancer Therapies: Incidence and Clinical Significance," Drug Safety, 2000 (5): 381-390.
Office Action issued in U.S. Appl. No. 13/619,280 dated Oct. 28, 2013.

* cited by examiner

DIARYLHYDANTOIN COMPOUNDS

This application claims the benefit of U.S. Provisional Application No. 60/996,076, filed Oct. 26, 2007, the specification of which is hereby incorporated by reference.

The present invention relates to diarylhydantoin compounds including diarylthiohydantoins, and methods for synthesizing them and using them in the treatment of hormone refractory prostate cancer. This invention was made with Government support under Grant No. CA092131 awarded by the National Institutes of Health. The Government has certain rights in this invention.

FIELD OF THE INVENTION

Background of the Invention

Prostate cancer is the most common incidence of cancer and the second leading cause of cancer death in Western men. When the cancer is confined locally, the disease can be cured by surgery or radiation. However, 30% of such cancer relapses with distant metastatic disease and others have advanced disease at diagnoses. Advanced disease is treated by castration and/or administration of antiandrogens, the so-called androgen deprivation therapy. Castration lowers the circulating levels of androgens and reduces the activity of androgen receptor (AR). Administration of antiandrogens blocks AR function by competing away androgen binding, therefore, reducing the AR activity. Although initially effective, these treatments quickly fail and the cancer becomes hormone refractory.

Nonsteroidal anti-androgens, such as bicalutamide, have been preferred over steroidal compounds for prostate cancer because they are more selective and have fewer side effects. This class of compounds has been described in patents such as U.S. Pat. No. 4,097,578, U.S. Pat. No. 5,411,981, U.S. Pat. No. 5,705,654, PCT International Applications WO 97/00071 and WO 00/17163, and U.S. Published Patent Application Number 2004/0009969, all of which are hereby incorporated by reference. Bicalutamide (brand name: Casodex) is the most commonly used anti-androgen. While it has an inhibitory effect on AR in hormone sensitive prostate cancer, it fails to suppress AR when cancer becomes hormone refractory.

U.S. Pat. No. 5,434,176 includes broad claims which encompass a very large number of compounds, but synthetic routes are only presented for a small fraction of these compounds and pharmacological data are only presented for two of them, and one skilled in the art could not readily envision other specific compounds. U.S. Pat. No. 5,434,176 is hereby incorporated by reference.

SUMMARY OF THE INVENTION

The invention provides a series of compounds having strong antagonistic activities with minimal agonistic activities against androgen receptor (AR). These compounds inhibit the growth of hormone refractory prostate cancer.

The invention includes a compound having the formula

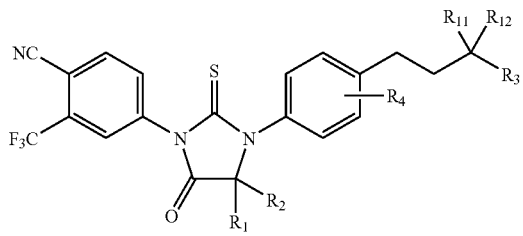

$R_1$ and $R_2$ together can include eight or fewer carbon atoms and can be selected from the group consisting of alkyl, substituted alkyl, and, together with the carbon to which they are linked, a cycloalkyl or substituted cycloalkyl group. $R_3$ can be hydrogen, cyano, formyl,

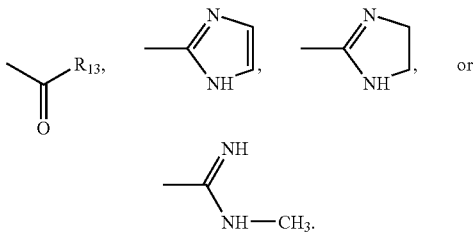

$R_4$ can be hydrogen, F, Cl, Br, or I. $R_{11}$ and $R_{12}$ can be the same or different and are hydrogen or methyl. $R_{13}$ can be hydrogen or —$NR_{14}R_{15}$. $R_{14}$ and $R_{15}$ can be the same or different and are hydrogen or methyl.

For example, $R_1$ and $R_2$ can be independently methyl or, together with the carbon to which they are linked, cyclobutyl or cyclopentyl. For example, $R_{11}$ and $R_{12}$ can be both hydrogen or both methyl. For example, $R_{13}$ can be —$NH(CH_3)$ or —$N(CH_3)_2$. For example, when $R_4$, $R_{11}$, and $R_{12}$ are each hydrogen and when $R_1$ and $R_2$ together with the carbon to which they are linked are cyclobutyl, then $R_3$ can be other than cyano and

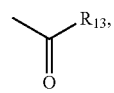

with $R_{13}$ hydrogen, —$NH_2$, —$NH(CH_3)$, or —$N(CH_3)_2$.

The invention provides a pharmaceutical composition comprising a therapeutically effective amount of a compound according to any of the preceding compounds or a pharmaceutically acceptable salt thereof, and a pharmaceutically acceptable carrier or diluent.

The invention encompasses a method for treating a hyperproliferative disorder comprising administering such a pharmaceutical composition to a subject in need of such treatment, thereby treating the hyperproliferative disorder. The hyperproliferative disorder may be hormone refractory prostate cancer. The dosage may be in the range of from about 0.001 mg per kg body weight per day to about 100 mg per kg body weight per day, about 0.01 mg per kg body weight per day to about 100 mg per kg body weight per day, about 0.1 mg per kg body weight per day to about 10 mg per kg body weight per day, or about 1 mg per kg body weight per day.

The compound may be administered by intravenous injection, by injection into tissue, intraperitoneally, orally, or nasally. The composition may have a form selected from the group consisting of a solution, dispersion, suspension, powder, capsule, tablet, pill, time release capsule, time release tablet, and time release pill.

The invention provides a method of synthesizing a diaryl compound of formula:

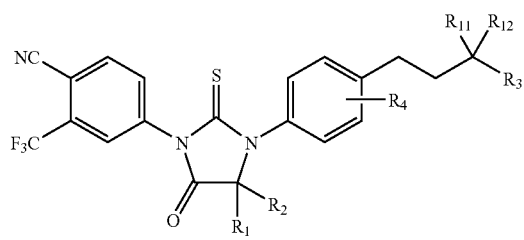

The method includes mixing Compound I

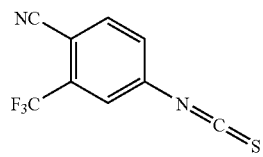
Compound I with Compound II

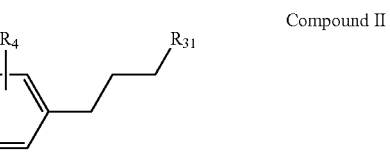
Compound II in a first polar solvent to form a mixture. The method further includes the following: adding a second polar solvent, the same as or different from the first polar solvent, and an aqueous acid to the mixture; refluxing the mixture; cooling the mixture and combining with water; and separating the diaryl compound from the mixture. $R_{31}$ is cyano, carboxy,

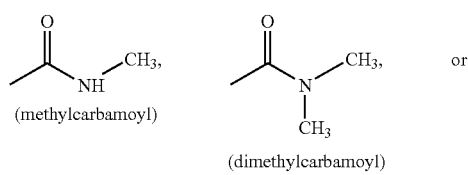

(methylcarbamoyl)     (dimethylcarbamoyl)

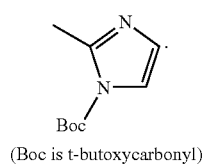

(Boc is t-butoxycarbonyl)

$R_{32}$ is

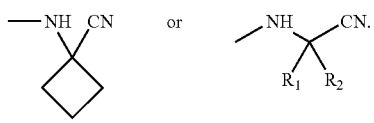

$R_1$ and $R_2$ together include eight or fewer carbon atoms and are alkyl, substituted alkyl, or, together with the carbon to which they are linked, a cycloalkyl or substituted cycloalkyl group. $R_3$ is hydrogen, cyano, formyl,

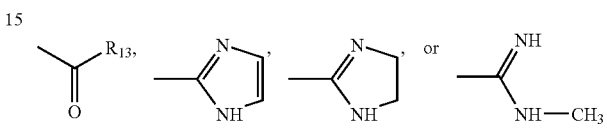

$R_4$ is hydrogen, F, Cl, Br, or I. $R_{11}$ and $R_{12}$ can be the same or different and are hydrogen or methyl. $R_{13}$ is hydrogen or $-NR_{14}R_{15}$. $R_{14}$ and $R_{15}$ can be the same or different and are hydrogen or methyl.

The compounds presented are expected to have substantial androgen receptor antagonist activity and no substantial agonist activity on hormone refractory prostate cancer cells.

The invention encompasses a method comprising providing at least one such compound, measuring inhibition of androgen receptor activity for the compound and determining if the inhibition is above a first predetermined level, measuring stimulation of androgen receptor activity in hormone refractory cancer cells for the compound and determining if the stimulation is below a second predetermined level, and selecting the compound if the inhibition is above the first predetermined level and the stimulation is below the second predetermined level. The predetermined levels may be those of bicalutamide. The step of measuring inhibition may comprise measuring inhibitory concentration (IC50) in an AR response reporter system or a prostate specific antigen secreting system. The step of measuring stimulation may comprise measuring fold induction by increasing concentrations in an AR response reporter system or a prostate specific antigen secreting system. The method of measuring inhibition and/or stimulation may comprise measuring an effect of the compound on tumor growth in an animal.

DETAILED DESCRIPTION

Embodiments of the invention are discussed in detail below. In describing embodiments, specific terminology is employed for the sake of clarity. However, the invention is not intended to be limited to the specific terminology so selected. A person skilled in the relevant art will recognize that other equivalent parts can be employed and other methods developed without parting from the spirit and scope of the invention. All references cited herein are incorporated by reference as if each had been individually incorporated.

Recently, overexpression of AR has been identified and validated as a cause of hormone refractory prostate cancer. See Chen, C. D., Welsbie, D. S., Tran, C., Baek, S. H., Chen, R., Vessella, R., Rosenfeld, M. G., and Sawyers, C. L., Molecular determinants of resistance to antiandrogen therapy, Nat. Med., 10: 33-39, 2004, which is hereby incorporated by reference. Overexpression of AR is sufficient to cause progression from hormone sensitive to hormone refractory prostate cancer, suggesting that better AR inhibitors than the current drugs can slow the progression of prostate cancer. It was demonstrated that AR and its ligand binding are necessary for growth of hormone refractory prostate cancer, indicating that AR is still a target for this disease. It was also demonstrated that overexpression of AR converts anti-androgens from antagonists to agonists in hormone refractory prostate cancer (an AR antagonist inhibits AR activity and an AR agonist stimulates AR activity). Data from this work explains why castration and anti-androgens fail to prevent prostate cancer progression and reveals unrecognized properties of hormone refractory prostate cancer.

Two weaknesses of current antiandrogens are blamed for the failure to prevent prostate cancer progression from the hormone sensitive stage to the hormone refractory disease and to effectively treat hormone refractory prostate cancer. One is their weak antagonistic activities and the other is their strong agonistic activities when AR is overexpressed in hormone refractory prostate cancer. Better AR inhibitors with more potent antagonistic activities and minimal agonistic activities are needed to delay disease progression and to treat the fatal hormone refractory prostate cancer.

Some new properties of hormone refractory prostate cancer are reported in PCT applications US04/42221 and US05/05529, which are hereby incorporated by reference. PCT International Application US05/05529 presented a methodology for identifying androgen receptor antagonist and agonist characteristics of compounds.

Synthesis of Diarylhydantoin Compounds

The invention provides for synthesis of diarylthiohydantoin compounds having the formula

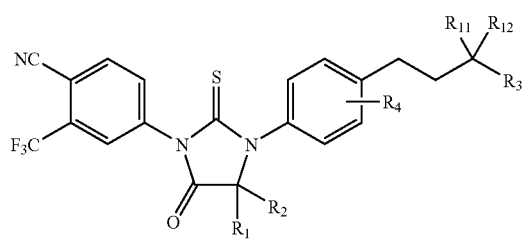

R1 and R2 together can comprise eight or fewer carbon atoms and can be alkyl, substituted alkyl, or, together with the carbon to which they are linked, a cycloalkyl or substituted cycloalkyl group. R3 can be hydrogen, cyano, formyl,

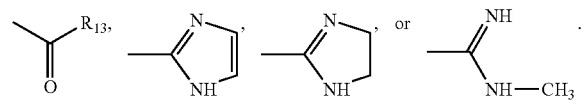

$R_4$ can be hydrogen, F, Cl, Br, and I. $R_{11}$ and $R_{12}$ can be the same or different and can be hydrogen or methyl. $R_{13}$ can be hydrogen or —$NR_{14}R_{15}$. $R_{14}$ and $R_{15}$ can be the same or different and can be hydrogen or methyl.

Definitions

As used herein, the term "alkyl" denotes branched or unbranched hydrocarbon chains, preferably having about 1 to about 8 carbons, such as, methyl, ethyl, n-propyl, iso-propyl, n-butyl, sec-butyl, iso-butyl, tert-butyl, 2-methylpentyl pentyl, hexyl, isohexyl, heptyl, 4,4-dimethyl pentyl, octyl, 2,2,4-trimethylpentyl and the like. "Substituted alkyl" includes an alkyl group optionally substituted with one or more functional groups which may be attached to such chains, such as, hydroxyl, bromo, fluoro, chloro, iodo, mercapto or thio, cyano, alkylthio, heterocyclyl, aryl, heteroaryl, carboxyl, carbalkoyl, alkyl, alkenyl, nitro, amino, alkoxyl, amido, and the like to form alkyl groups such as trifluoro methyl, 3-hydroxyhexyl, 2-carboxypropyl, 2-fluoroethyl, carboxymethyl, cyanobutyl and the like.

Unless otherwise indicated, the term "cycloalkyl" as employed herein alone or as part of another group includes saturated or partially unsaturated (containing 1 or more double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl. "Substituted cycloalkyl" includes a cycloalkyl group optionally substituted with 1 or more substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol and/or alkylthio and/or any of the substituents included in the definition of "substituted alkyl." For example,

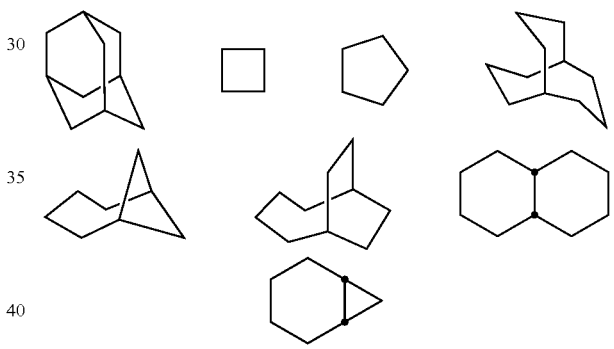

and the like.

Unless otherwise indicated, the term "alkenyl" as used herein by itself or as part of another group refers to straight or branched chain radicals of 2 to 20 carbons, preferably 2 to 12 carbons, and more preferably 2 to 8 carbons in the normal chain, which include one or more double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like. "Substituted alkenyl" includes an alkenyl group optionally substituted with one or more substituents, such as the substituents included above in the definition of "substituted alkyl" and "substituted cycloalkyl."

Unless otherwise indicated, the term "alkynyl" as used herein by itself or as part of another group refers to straight or branched chain radicals of 2 to 20 carbons, preferably 2 to 12 carbons and more preferably 2 to 8 carbons in the normal chain, which include one or more triple bonds in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like. "Substituted alkynyl" includes an alkynyl group optionally substituted with one or more substituents, such as the substituents included above in the definition of "substituted alkyl" and "substituted cycloalkyl."

The terms "arylalkyl", "arylalkenyl" and "arylalkynyl" as used alone or as part of another group refer to alkyl, alkenyl and alkynyl groups as described above having an aryl substituent. Representative examples of arylalkyl include, but are not limited to, benzyl, 2-phenylethyl, 3-phenylpropyl, phenethyl, benzhydryl and naphthylmethyl and the like. "Substituted arylalkyl" includes arylalkyl groups wherein the aryl portion is optionally substituted with one or more substituents, such as the substituents included above in the definition of "substituted alkyl" and "substituted cycloalkyl."

The terms "arylalkyl", "arylalkenyl" and "arylalkynyl" as used alone or as part of another group refer to alkyl, alkenyl and alkynyl groups as described above having an aryl substituent. Representative examples of arylalkyl include, but are not limited to, benzyl, 2-phenylethyl, 3-phenylpropyl, phenethyl, benzhydryl and naphthylmethyl and the like. "Substituted arylalkyl" includes arylalkyl groups wherein the aryl portion is optionally substituted with one or more substituents, such as the substituents included above in the definition of "substituted alkyl" and "substituted cycloalkyl."

The term "halogen" or "halo" as used herein alone or as part of another group refers to chlorine, bromine, fluorine, and iodine.

The terms "halogenated alkyl", "halogenated alkenyl" and "alkynyl" as used herein alone or as part of another group refers to "alkyl", "alkenyl" and "alkynyl" which are substituted by one or more atoms selected from fluorine, chlorine, bromine, and iodine.

Unless otherwise indicated, the term "aryl" or "Ar" as employed herein alone or as part of another group refers to monocyclic and polycyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings).

"Substituted aryl" includes an aryl group optionally substituted with one or more functional groups, such as halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl and/or any of the alkyl substituents set out herein.

Unless otherwise indicated, the term "heterocyclic" or "heterocycle", as used herein, represents an unsubstituted or substituted stable 5- to 10-membered monocyclic ring system which may be saturated or unsaturated, and which consists of carbon atoms and from one to four heteroatoms selected from N, O or S, and wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocyclic groups include, but is not limited to, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isooxazolyl, isoxazolidinyl, morpholinyl, thiazolyl, thiazolidinyl, isothiazolyl, thiadiazolyl, tetrahydropyranyl, thiamorpholinyl, thiamorpholinyl sulfoxide, thiamorpholinyl sulfone, and oxadiazolyl. The term "heterocyclic aromatic" as used here in alone or as part of another group refers to a 5- or 7-membered aromatic ring which includes 1, 2, 3 or 4 hetero atoms such as nitrogen, oxygen or sulfur and such rings fused to an aryl, cycloalkyl, heteroaryl or heterocycloalkyl ring (e.g. benzothiophenyl, indolyl), and includes possible N-oxides. "Substituted heteroaryl" includes a heteroaryl group optionally substituted with 1 to 4 substituents, such as the substituents included above in the definition of "substituted alkyl" and "substituted cycloalkyl." Examples of heteroaryl groups include the following:

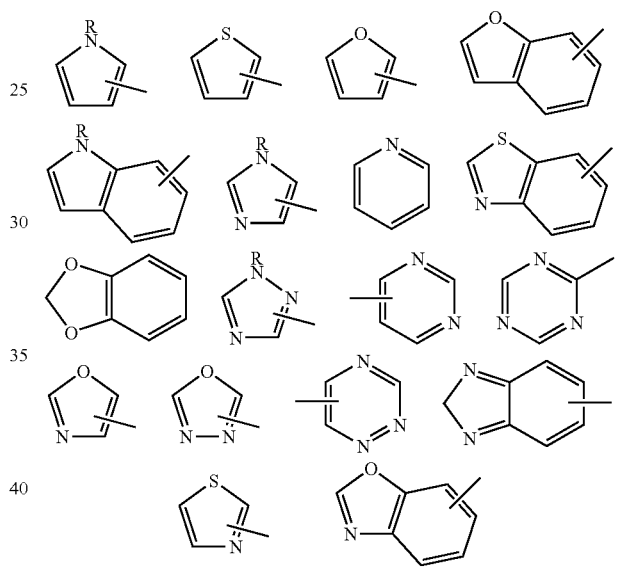

and the like.

Materials were obtained from commercial suppliers and were used without further purification. Air or moisture sensitive reactions were conducted under argon atmosphere using oven-dried glassware and standard syringe/septa techniques. The reactions were monitored with a silica gel TLC plate under UV light (254 nm) followed by visualization with a p-anisaldehyde or ninhydrin staining solution. Column chromatography was performed on silica gel 60. $^1$H NMR spectra were measured at 400 MHz in $CDCl_3$ unless stated otherwise and data were reported as follows in ppm (δ) from the internal standard (TMS, 0.0 ppm): chemical shift (multiplicity, integration, coupling constant in Hz.).

Synthesis of ND-1

4-[4-(t-Butoxycarbonylamino)phenyl]butanoic Acid
(100)

Di-tert-butyl dicarbonate (0.73 g, 3.35 mmol) was added to a solution of 4-(4-aminophenyl)butyric acid (0.5 g, 2.79 mmol) and sodium hydroxide (0.14 g, 3.35 mmol) in tert-butanol (5 mL) and water (5 mL) at 0° C. The mixture was warmed to room temperature and stirred for 9 h. The mixture was partitioned with diethyl ether (20 mL) and water (20 mL) and then the aqueous layer was acidified to pH 2-3 by 1 N KHSO₄ solution. The aqueous mixture extracted with ethyl acetate (3×20 mL) and the organic layer was dried over MgSO₄, concentrated to give crude 4-[4-(t-Butoxycarbonylamino)phenyl]butanoic acid (100) (0.73 g, 94%) which was used without further purification.

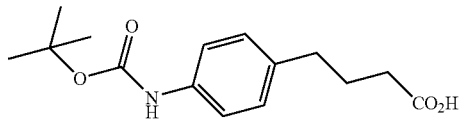 [SMILES: CC(C)(C)OC(=O)Nc1ccc(CCCC(=O)O)cc1]

¹H NMR δ 7.26 (d, 2H, J=8.5 Hz) 7.10 (d, 2H, J=8.5 Hz) 6.48 (br s, 1H), 2.62 (t, 2H, J=7.5 Hz), 2.33 (t, 2H, J=7.5 Hz) 1.93 (p, 2H, J=7.5 Hz).

4-[4-(t-Butoxycarbonylamino)phenyl]butanamide (99)

Thionyl chloride (0.22 mL, 3.01 mmol) was added slowly to a solution of 4-[4-(t-Butoxycarbonylamino)phenyl]butanoic acid (100) (0.70 g, 2.51 mmol) in DMF (5 mL) cooled at −5° C. The mixture was stirred for an additional 1 h at −5° C. Excess ammonia (freshly distilled from its aqueous solution) was added to the reaction medium. The second mixture was stirred for an additional 1 h. Ethyl acetate (50 mL) was added to the mixture, which was washed with brine (2×50 mL). The organic layer was dried over MgSO₄, concentrated and the residue was purified by silica gel column chromatography (dichloromethane:acetone, 9:1) to give 4-[4-(t-Butoxycarbonylamino)phenyl]butanamide (99) (0.57 g, 82%) as a white solid.

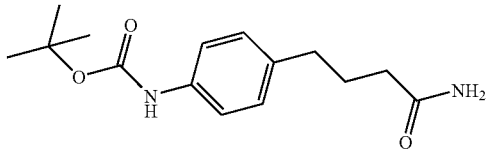 [SMILES: CC(C)(C)OC(=O)Nc1ccc(CCCC(N)=O)cc1]

¹H NMR δ 7.26 δ, 2H, J=8.4 Hz), 7.09 (d, 2H, J=8.4 Hz) 6.48 (br s, 1H), 5.47 (br s, 2H), 2.62 (t, 2H, J=7.4 Hz) 2.20 (t, 2H, J=7.4 Hz) 1.94 (p, 2H, J=7.4 Hz) 1.51 (s, 9H).

4-[4-(t-Butoxycarbonylamino)phenyl]butanenitrile (98)

A solution of DMSO (0.13 mL, 1.84 mmol) in dichloromethane (2 mL) was added to a stirred solution of oxalyl chloride (0.12 mL, 1.38 mmol) in dichloromethane (2 mL) at −78° C. After 15 min, a dichloromethane (1 mL) solution of 2 (0.32 g, 1.15 mmol) was added to the reaction mixture. Stirring was continued for 20 min at −78° C., and then triethylamine (0.48 mL, 3.45 mmol) was added. After 30 min, the reaction mixture was warmed to room temperature and then reaction was quenched with saturated aq. NH₄Cl solution. The mixture was partitioned with diethyl ether (30 mL) and water (20 mL). The organic layer was dried over MgSO₄, concentrated and the residue was purified by silica gel column chromatography (hexane:ethyl acetate, 4:1) to give 4-[4-(t-Butoxycarbonylamino)phenyl]butanenitrile (98) (0.22 g, 73%) as a white solid.

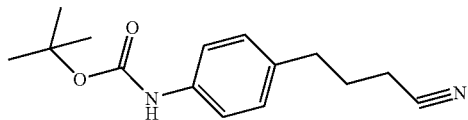 [SMILES: CC(C)(C)OC(=O)Nc1ccc(CCCC#N)cc1]

¹H NMR δ 7.30 (d, 2H, J=8.4 Hz) 6.10 (d, 2H, J=8.4 Hz) 6.42 (br s, 1H), 2.73 (t, 2H, J=7.3 Hz), 2.30 (t, 2H, J=7.3 Hz) 1.95 (p, 2H, J=7.3 Hz) 1.52 (s, 9H).

4-(4-Aminophenyl)butanenitrile (97)

A 0.25 M solution of trifluoroacetic acid in dichloromethane (5 mL, 1.25 mmol) was added to 4-[4-(t-Butoxycarbonylamino)phenyl]butanenitrile (98) (0.22 g, 0.85 mmol). After 30 min, reaction was quenched with 1 N NaOH solution. The mixture was partitioned with ethyl acetate (30 mL) and water (20 mL). The organic layer was dried over MgSO₄, concentrated to give 4-(4-Aminophenyl)butanenitrile (97) (0.16 g, 99%) which was used without further purification.

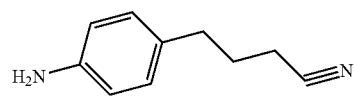 [SMILES: N#CCCCc1ccc(N)cc1]

¹H NMR δ 6.97 (d, 2H, J=8.5 Hz) 6.64 (d, 2H, J=8.5 Hz) 3.59 (br s, 2H), 2.67 (t, 2H, J=7.3 Hz), 2.29 (t, 2H, J=7.3 Hz) 1.92 (p, 2H, J=7.3 Hz).

4-Isothiocyanato-2-trifluoromethylbenzonitrile (96)

4-Amino-2-trifluoromethylbenzonitrile (2.23 g, 12 mmol) was added portionwise over 15 min into a well-stirred heterogeneous mixture of thiophosgene (1 mL, 13 mmol) in water (22 mL) at room temperature. Stirring was continued for an additional 1 h. The reaction medium was extracted with chloroform (3×15 mL). The combined organic phase was dried over MgSO₄ and evaporated to dryness under reduced pressure to yield desired product 4-Isothiocyanato-2-trifluoromethylbenzonitrile (96) (2.72 g, 11.9 mmol, 99%) as brownish solid and was used without further purification.

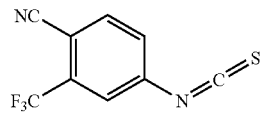

¹H NMR δ 7.84 (d, 1H, J=8.3 Hz) 7.59 (d, 1H, J=2.1 Hz) 7.49 (dd, 1H, J=8.3, 2.1 Hz).

4-[4-(1-Cyanodimethylamino)phenyl]butanenitrile (95)

A mixture of 4-(4-Aminophenyl)butanenitrile (97) (50 mg, 0.26 mmol), acetone cyanohydrin (0.15 mL, 1.58 mmol) was heated to 80° C. and stirred for 12 h. To the medium was added ethyl acetate (20 mL) and then washed with water (2×20 mL). The organic layer was dried over MgSO₄, concentrated and the residue was purified by silica gel column chromatography (hexane:ethyl acetate, 1:1) to give 4-[4-(1-Cyanodimethylamino)phenyl]butanenitrile (95) (52 mg, 87%) as a white solid.

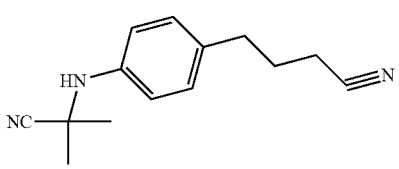

¹H NMR δ 7.07 (d, 2H, J=8.3 Hz) 6.87 (d, 2H, J=8.3 Hz) 3.68 (br s, 1H), 2.70 (t, 2H, J=7.3 Hz), 2.31 (t, 2H, J=7.3 Hz) 1.94 (p, 2H, J=7.3 Hz) 1.69 (s, 6H).

4-(3-(4-(3-Cyanopropyl)phenyl)-4,4-dimethyl-5-oxo-2-thioxo-imidazolidin-1-yl)-2-(trifluoromethyl)benzonitrile (94) [ND-1]

A mixture of 4-Isothiocyanato-2-trifluoromethylbenzonitrile (96) (32 mg, 0.14 mmol) and 4-[4-(1-Cyanodimethylamino)phenyl]butanenitrile (95) (16 mg, 0.07 mmol) in DMF (1 mL) was heated under microwave irradiation at 80° C. for 6 h. To this mixture was added methanol (10 mL) and aq. 1 N HCl (3 mL). The second mixture was refluxed for 1.5 h. After being cooled to room temperature, the reaction mixture was poured into cold water (20 mL) and extracted with ethyl acetate (30 mL). The organic layer was dried over MgSO₄, concentrated and the residue was purified by silica gel column chromatography (hexane:ethyl acetate, 2:1) to give 4-(3-(4-(3-Cyanopropyl)phenyl)-4,4-dimethyl-5-oxo-2-thioxo-imidazolidin-1-yl)-2-(trifluoromethyl)benzonitrile (94) [ND-1] (20 mg, 62%) as a white solid.

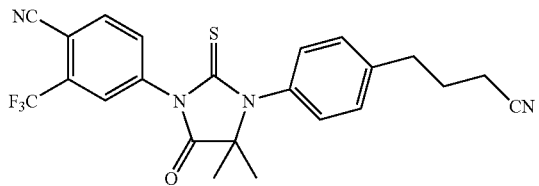

¹H NMR δ 7.98 (d, 1H, J=8.3 Hz) 7.97 (d, 1H, J=1.8 Hz) 7.85 (dd, 1H, J=8.3, 1.8 Hz), 7.37 (d, 2H, J=8.3 Hz) 7.25 (d, 2H, J=8.3 Hz) 2.87 (t, 2H, J=7.0 Hz) 2.40 (t, 2H, J=7.0 Hz) 2.05 (p, 2H, J=7.0 Hz) 1.59 (s, 6H).

Synthesis of ND-2

4-[4-(1-Cyanocyclopentyl amino)phenyl]butanenitrile (93)

A mixture of 4-(4-Aminophenyl)butanenitrile (97) (52 mg, 0.27 mmol), cyclopentanone (0.07 mL, 0.55 mmol) and TMSCN (0.05 mL, 0.55 mmol) was heated to 80° C. and stirred for 13 h. To the medium was added ethyl acetate (2×20 mL) and then washed with water (2×20 mL). The organic layer was dried over MgSO₄, concentrated and the residue was purified with silica gel column chromatography (hexane:ethyl acetate, 1:1) to give 4-[4-(1-Cyanocyclopentyl amino)phenyl]butanenitrile (93) (70 mg, quant.) as a white solid.

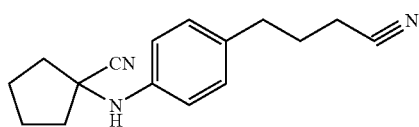 [SMILES: N#CCCCc1ccc(NC2(C#N)CCCC2)cc1]

¹H NMR δ 7.06 (d, 2H, J=8.3 Hz) 6.78 (d, 2H, J=8.3 Hz) 3.80 (br s, 1H), 2.70 (t, 2H, J=7.3 Hz), 2.34-2.42 (m, 2H), 2.31 (t, 2H, J=7.3 Hz) 2.09-2.18 (m, 2H), 1.94 (p, 2H, J=7.3 Hz) 1.86-1.91 (m, 4H).

4-(1-(4-(3-Cyanopropyl)phenyl)-4-oxo-2-thioxo-1,3-diazaspiro[4.4]non-3-yl)-2-trifluoromethylbenzonitrile (92) [ND-2]

A mixture of 4-Isothiocyanato-2-trifluoromethylbenzonitrile (96) (36 mg, 0.16 mmol) and 4-[4-(1-Cyanocyclopentyl amino)phenyl]butanenitrile (93) (20 mg, 0.08 mmol) in DMF (1 mL) was heated under microwave irradiation at 80° C. for 6 h. To this mixture was added methanol (10 mL) and aq. 1 N HCl (3 mL). The second mixture was refluxed for 1.5 h. After being cooled to room temperature, the reaction mixture was poured into cold water (20 mL) and extracted with ethyl acetate (30 mL). The organic layer was dried over MgSO₄, concentrated and the residue was purified by silica gel column chromatography (hexane:ethyl acetate, 2:1) to give 4-(1-(4-(3-Cyanopropyl)phenyl)-4-oxo-2-thioxo-1,3-diazaspiro[4.4]non-3-yl)-2-trifluoromethylbenzonitrile (92) [ND-2]

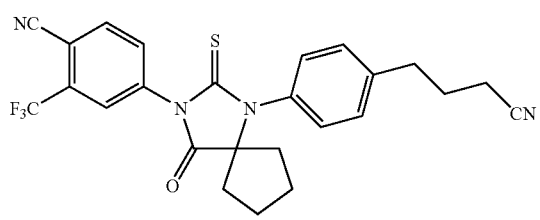

(25 mg, 65%) as a white solid. ¹H NMR δ 7.98 (d, 1H, J=1.8 Hz) 7.97 (d, 1H, J=8.3 Hz) 7.86 (dd, 1H, J=8.3, 1.8 Hz), 7.37 (d, 2H, J=8.3 Hz) 7.27 (d, 2H, J=8.3 Hz) 2.87 (t, 2H, J=7.3 Hz), 2.40 (t, 2H, J=7.3 Hz) 2.28-2.35 (m, 2H), 2.14-2.23 (m, 2H), 2.05 (p, 2H, J=7.3 Hz) 1.85-1.92 (m, 2H), 1.48-1.55 (m, 2H).

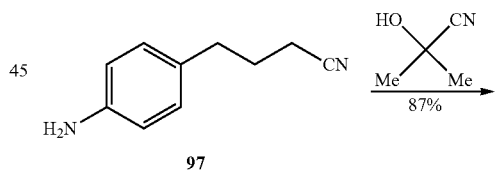

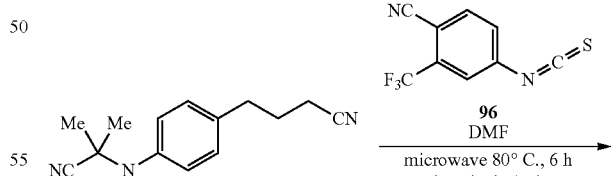

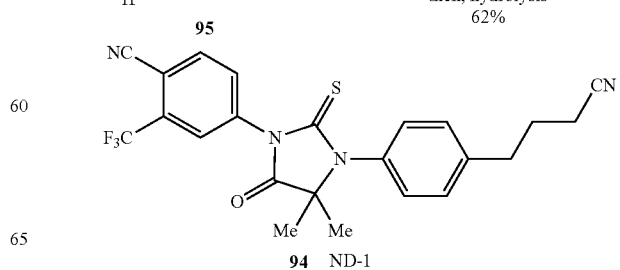

-continued

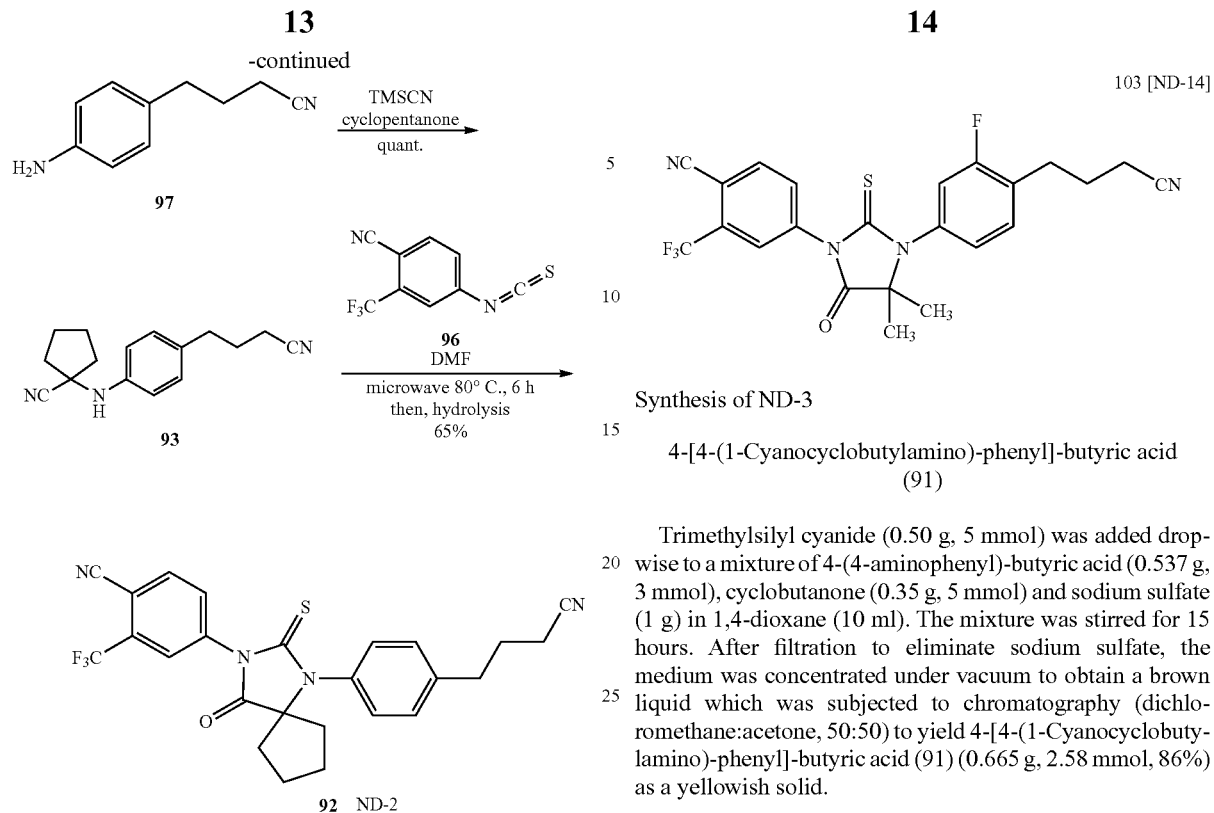

Synthesis of ND-14

4-(3-(4-(3-Cyanopropyl)-3-fluorophenyl)-4,4-dimethyl-5-oxo-2-thioxo-imidazolidin-1-yl)-2-(trifluoromethyl)benzonitrile (103)

4-(3-(4-(3-Cyanopropyl)-3-fluorophenyl)-4,4-dimethyl-5-oxo-2-thioxo-imidazolidin-1-yl)-2-(trifluoromethyl)benzonitrile (103) [ND-14] can be synthesized in a manner similar as to that for synthesizing (92) [ND-2]. A mixture of 4-Isothiocyanato-2-trifluoromethylbenzonitrile (96) and 4-(4-(2-cyanopropan-2-ylamino)-2-fluorophenyl)butanenitrile (101) in solvent, for example, in DMF, is heated under microwave irradiation at 80° C. for 6 h.

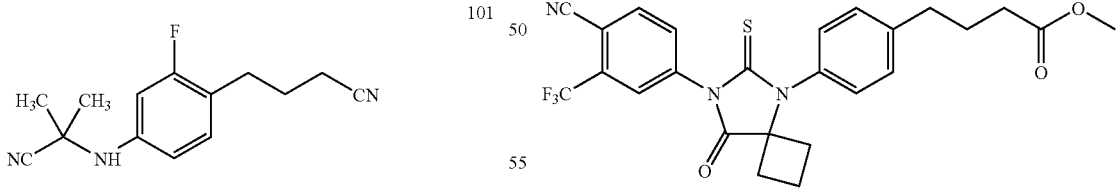

To this mixture is added alcohol, e.g., methanol, and acid, e.g., aqueous hydrochloric acid. The second mixture is refluxed for 1.5 h. After being cooled to room temperature, the reaction mixture is poured into cold water and extracted, for example, with ethyl acetate. The organic layer is dried, e.g., dried over MgSO$_4$, concentrated, and the residue is purified, for example, by silica gel column chromatography using hexane:ethyl acetate (2:1), to give 4-(3-(4-(3-Cyanopropyl)-3-fluorophenyl)-4,4-dimethyl-5-oxo-2-thioxo-imidazolidin-1-yl)-2-(trifluoromethyl)benzonitrile (103) [ND-14].

Synthesis of ND-3

4-[4-(1-Cyanocyclobutylamino)-phenyl]-butyric acid (91)

Trimethylsilyl cyanide (0.50 g, 5 mmol) was added dropwise to a mixture of 4-(4-aminophenyl)-butyric acid (0.537 g, 3 mmol), cyclobutanone (0.35 g, 5 mmol) and sodium sulfate (1 g) in 1,4-dioxane (10 ml). The mixture was stirred for 15 hours. After filtration to eliminate sodium sulfate, the medium was concentrated under vacuum to obtain a brown liquid which was subjected to chromatography (dichloromethane:acetone, 50:50) to yield 4-[4-(1-Cyanocyclobutylamino)-phenyl]-butyric acid (91) (0.665 g, 2.58 mmol, 86%) as a yellowish solid.

4-{4-[7-(4-cyano-3-trifluoromethylphenyl)-8-oxo-6-thioxo-5,7-diazaspiro[3.4]oct-5-yl]-phenyl}-butyric Acid Methyl Ester (90) [ND-4]

A mixture of 4-isothiocyanato-2-trifluoromethylbenzonitrile (96) (0.547 g, 2.4 mmol) and 4-[4-(1-Cyanocyclobutylamino)-phenyl]-butyric acid (91) (0.342 g, 1.5 mmol) in dry DMF (2 ml) was stirred at room temperature for 15 hours. To this mixture were added methanol (10 ml) and HCl aq. (5 ml, 2M). The second mixture was refluxed for 3 h. After being cooled to room temperature, the reaction mixture was poured into cold water (10 ml) and extracted with ethyl acetate (3×30 ml). The organic layer was dried over MgSO$_4$, concentrated and chromatographed (dichloromethane) to yield 4-{4-[7-(4-cyano-3-trifluoromethylphenyl)-8-oxo-6-thioxo-5,7-diazaspiro[3.4]oct-5-yl]-phenyl}-butyric acid methyl ester (90) [ND-4] (0.594 g, 1.18 mmol, 79%) as a white powder.

$^1$H NMR (CDCl$_3$, 400 MHz) δ 1.60-1.70 (m, 1H), 1.98-2.07 (m, 2H), 2.14-2.26 (m, 1H), 2.40 (t, J=7.4 Hz, 2H), 2.52-2.60 (m, 2H), 2.62-2.68 (m, 2H), 2.74 (t, J=7.4 Hz, 2H), 3.68 (s, 3H), 7.22 (d, J=8.2 Hz, 2H), 7.38 (d, J=8.2 Hz, 2H), 7.86 (dd, J$_1$=8.3 Hz, J$_2$=1.8 Hz, 1H), 7.95 (d, J=8.3 Hz, 1H), 7.98 (d, J=1.8 Hz, 1H); $^{13}$C NMR (CDCl$_3$, 100 MHz) δ 13.7, 26.1, 31.4, 33.5, 34.8, 51.7, 67.5, 109.9, 114.9, 121.9 (q, J=272.7 Hz), 127.1 (q, J=4.7 Hz), 129.7, 130.1, 132.3, 133.0, 133.3 (q, J=33.2 Hz), 135.2, 137.2, 143.5, 173.8, 175.0, 179.9.

4-{4-[7-(4-cyano-3-trifluoromethylphenyl)-8-oxo-6-thioxo-5,7-diaza-spiro[3.4]oct-5-yl]-phenyl}-butyric Acid (89) [ND-5]

A mixture of 4-{4-[7-(4-cyano-3-trifluoromethylphenyl)-8-oxo-6-thioxo-5,7-diazaspiro[3.4]oct-5-yl]-phenyl}-butyric acid methyl ester (90) [ND-4] (0.501 g, 1 mmol) in methanol (10 ml) and solution of sodium hydroxide (10 ml, 2M) was stirred at room temperature for 5 hours. The methanol was evaporated. The residue was adjusted to pH=5 by HCl aq. (2M) and then, the medium was extracted with ethyl acetate (3×50 ml). The organic layer was dried over MgSO₄ and concentrated to dryness to obtain 4-{4-[7-(4-cyano-3-trifluoromethylphenyl)-8-oxo-6-thioxo-5,7-diaza-spiro[3.4]oct-5-yl]-phenyl}-butyric acid (89) [ND-5] (0.482 g, 0.99 mmol, 99%), the structure of which is illustrated in Formula 89.

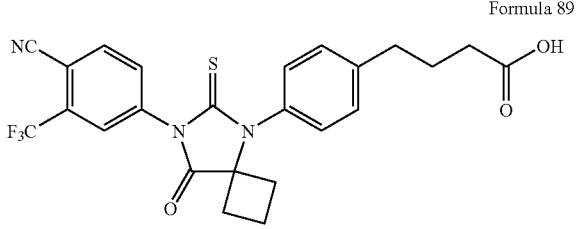

Formula 89

$^1$H NMR (CDCl₃, 400 MHz) δ 1.60-1.70 (m, 1H), 1.98-2.07 (m, 2H), 2.14-2.26 (m, 1H), 2.45 (t, J=7.3 Hz, 2H), 2.51-2.59 (m, 2H), 2.62-2.68 (m, 2H), 2.77 (t, J=7.3 Hz, 2H), 7.23 (d, J=8.1 Hz, 2H), 7.40 (d, J=8.1 Hz, 2H), 7.85 (dd, J=8.3, 1.8 Hz, 1H), 7.95 (d, J=8.3 Hz, 1H), 7.97 (d, J=1.8 Hz, 1H); $^{13}$C NMR (CDCl₃, 100 MHz) δ 13.7, 25.9, 31.4, 33.4, 34.7, 67.5, 109.9, 114.9, 121.9 (q, J=272.6 Hz), 127.1 (q, J=4.7 Hz), 129.8, 130.1, 132.3, 133.0, 133.4 (q, J=33.1 Hz), 135.2, 137.2, 143.3, 174.9, 178.9, 179.9.

42-5) 4-{4-[7-(4-Cyano-3-trifluoromethylphenyl)-8-oxo-6-thioxo-5,7-diaza-spiro[3.4]oct-5-yl]-phenyl}-N-methyl-butyramide (88) [ND-6]

To a suspension of 4-{4-[7-(4-cyano-3-trifluoromethylphenyl)-8-oxo-6-thioxo-5,7-diaza-spiro[3.4]oct-5-yl]-phenyl}-butyric acid (89) (0.097 g, 0.2 mmol) in THF (10 ml) at −5° C. was added thionyl chloride (0.019 ml, 0.26 mmol). The medium was stirred at −5° C. for one hour. Then methylamine was bubbled into the mixture at −5° C. for 30 minutes. The medium was filtered. The filtrate was concentrated and chromatographed (dichloromethane:acetone, 75:25) to yield 4-{4-[7-(4-Cyano-3-trifluoromethylphenyl)-8-oxo-6-thioxo-5,7-diaza-spiro[3.4]oct-5-yl]-phenyl}-N-methyl-butyramide (88) [ND-6] (0.095 g, 0.19 mmol, 95%) as an off-white powder.

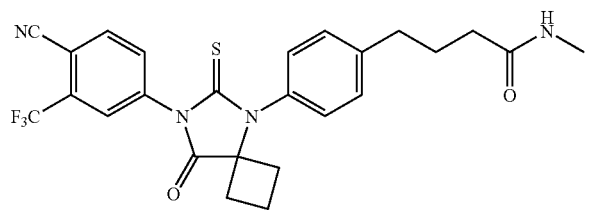

$^1$H NMR (CDCl₃, 400 MHz) δ 1.52-1.64 (m, 1H), 1.94-2.01 (m, 2H), 2.10-2.17 (m, 1H), 2.20 (t, J=7.3 Hz, 2H), 2.46-2.62 (m, 4H), 2.69 (t, J=7.3 Hz, 2H), 2.73 (d, J=4.7 Hz, 3H), 6.09 (bs, 1H), 7.16 (d, J=8.2 Hz, 2H), 7.33 (d, J=8.2 Hz, 2H), 7.82 (dd, J₁=8.3 Hz, J₂=1.8 Hz, 1H), 7.91 (d, J=8.3 Hz, 1H), 7.94 (d, J=1.8 Hz, 1H); $^{13}$C NMR (CDCl₃, 100 MHz) δ 13.7, 26.2, 26.8, 31.4, 35.0, 35.7, 67.5, 109.7, 114.9, 121.9 (q, J=272.7 Hz), 127.1 (q, J=4.7 Hz), 129.7, 130.0, 132.3, 133.8, 133.3 (q, J=33.2 Hz), 135.2, 137.3, 143.7, 173.3, 174.9, 179.8.

4-(4-(7-(4-Cyano-3-(trifluoromethyl)phenyl)-8-oxo-6-thioxo-5,7-diazaspiro[3.4]oct-an-5-yl)phenyl)-N-methylbutanimidamide (87) [ND-3]

To a solution of 4-{4-[7-(4-Cyano-3-trifluoromethylphenyl)-8-oxo-6-thioxo-5,7-diaza-spiro[3.4]oct-5-yl]-phenyl}-N-methyl-butyramide (88) [ND-6] (4.0 mg, 0.008 mmol) and pyridine (1.94 μL, 0.02 mmol) in dichloromethane (3 mL) at −40° C. was slowly added triflic anhydride (Tf₂O, 1.75 μL, 0.01 mmol). The mixture was allowed to warm to 0° C. over 3 h. The solution was then cooled to −40° C. and ammonia was introduced by bubbling. The reaction was then warmed to room temperature and stirred overnight. Without aqueous work up, flash chromatography using 10% methanol in ethyl acetate afforded 4-(4-(7-(4-Cyano-3-(trifluoromethyl)phenyl)-8-oxo-6-thioxo-5,7-diazaspiro[3.4]oct-an-5-yl)phenyl)-N-methylbutanimidamide (87) [ND-3] (2.9 mg, 72%) of as a colorless oil: 1H NMR (CD₃CN) δ 8.10 (d, 1H, J=8.2 Hz) 8.04 (s, 1H), 7.92 (d, 1H, J=8.2 Hz) 7.49 (br s, 2H), 7.43 (d, 2H, J=8.3 Hz), 7.30 (d, 2H, J=8.3 Hz) 3.26 (d, 3H, J=5.4 Hz) 2.77 (t, 2H, J=8.0 Hz) 2.56-2.65 (m, 2H), 2.52 (t, 2H, J=7.7 Hz) 2.42-2.52 (m, 2H), 1.95-2.12 (m, 3H), 1.47-1.62 (m, 1H).

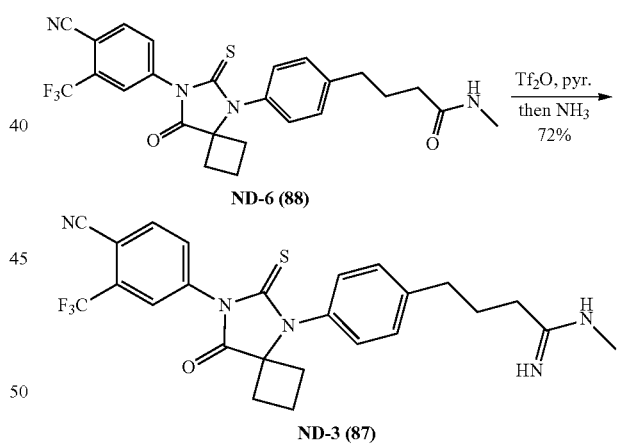

Synthesis of ND-7 and ND-8

Dimethyl 2-(2-fluoro-4-nitrophenyl)malonate (86)

To a suspension of sodium hydride (NaH, 60%, 0.40 g, 10.0 mmol) in dry DMF (10 mL) under ice cooling was added dimethyl malonate (1.04 mL, 9.1 mmol) dropwise followed by a solution of 1-bromo-2-fluoro-4-nitrobenzene (1.00 g, 4.55 mmol) in dry DMF (3 mL) under an argon atmosphere. The resulting mixture was stirred at 70° C. overnight and then allowed to cool to 21° C. The reaction mixture was quenched with saturated NH₄Cl and extracted with ethyl acetate (2×50 mL). The organic layer was dried over MgSO₄, concentrated and the residue was purified with silica gel column chromatography (hexane:ethyl acetate, 2:1) to give Dimethyl 2-(2-fluoro-4-nitrophenyl)malonate (86) (0.90 g, 73%) as a light yellowish solid: 1H NMR δ 8.07 (dd, 1H, J=8.6, 2.2 Hz), 7.98 (dd, 1H, J=9.3, 2.2 Hz), 7.74 (dd, 1H, J=8.6, 7.1 Hz), 5.08 (s, 1H), 3.81 (s, 6H).

Trimethyl 1-(2-fluoro-4-nitrophenyl)propane-1,1,3-tricarboxylate (85)

To a solution of the nitro diester, Dimethyl 2-(2-fluoro-4-nitrophenyl)malonate (86) (0.44 g, 1.62 mmol) and methyl acrylate (0.22 mL, 2.43 mmol) in absolute methanol (5 mL) was added a catalytic amount of sodium methoxide at 21° C. under argon. The reaction mixture was stirred for 40 h at the same temperature and then diluted with dichloromethane (50 mL). The resulting mixture was washed with water, brine and dried. The residue obtained upon evaporation of the solvents was purified on a silica gel (hexane:ethyl acetate, 8:1) to give Trimethyl 1-(2-fluoro-4-nitrophenyl)propane-1,1,3-tricarboxylate (85) (0.49 g, 85%): 1H NMR δ 8.04 (dd, 1H, J=8.7, 2.3 Hz), 7.95 (dd, 1H, J=10.9, 2.3 Hz), 7.57 (dd, 1H, J=8.7, 7.5 Hz), 3.81 (s, 6H), 3.62 (s, 3H), 2.64-2.69 (m, 2H), 2.35-2.40 (m, 2H).

Methyl 4-(2-fluoro-4-nitrophenyl)butanoate (84)

A solution of compound Trimethyl 1-(2-fluoro-4-nitrophenyl)propane-1,1,3-tricarboxylate (85) (0.23 g, 0.63 mmol), sodium chloride (0.11 g, 1.90 mmol) and water (0.15 mL) in distilled dimethylsulfoxide (4 mL) was heated to 155° C. overnight. The reaction mixture was allowed to cool to 21° C. and then worked up by adding water and extracting with ethyl acetate (2×50 mL). The organic layer was dried over $MgSO_4$, concentrated and the residue was purified with silica gel column chromatography (hexane:ethyl acetate, 8:1) to give desired Methyl 4-(2-fluoro-4-nitrophenyl)butanoate (84) (69 mg, 45%) and dimethyl 2-(2-fluoro-4-nitrophenyl)pentanedioate (83) (72 mg, 38%): 1H NMR of (10) δ 8.04 (dd, 1H, J=8.5, 2.2 Hz), 7.95 (dd, 1H, J=9.5, 2.2 Hz), 7.53 (dd, 1H, J=8.5, 7.1 Hz), 4.08 (t, 1H, J=7.6 Hz) 3.71 (s, 3H), 3.66 (s, 3H), 2.43-2.52 (m, 1H), 2.31-2.35 (m, 2H), 2.06-2.14 (m, 1H); 1H NMR of (84) δ 7.98 (dd, 1H, J=8.4, 2.2 Hz), 7.90 (dd, 1H, J=9.5, 2.2 Hz), 7.38 (dd, 1H, J=8.4, 7.3 Hz), 3.68 (s, 3H), 2.79 (t, 2H, J=7.7 Hz) 2.38 (t, 2H, J=7.3 Hz) 1.94-2.02 (m, 2H).

4-(2-Fluoro-4-nitrophenyl)butanoic Acid (82)

To a solution of Methyl 4-(2-fluoro-4-nitrophenyl)butanoate (84) (43 mg, 0.18 mmol) in methanol (1 mL) and water (3 mL) was added sodium hydroxide (0.18 g, 4.50 mmol). The reaction mixture was stirred at 21° C. overnight. The reaction mixture was quenched with 1 N HCl solution and extracted with ethyl acetate (2×30 mL). The organic layer was dried over $MgSO_4$, concentrated to give 4-(2-Fluoro-4-nitrophenyl)butanoic acid (82) (40 mg, 98%) and the residue was used without further purification.

4-(2-Fluoro-4-nitrophenyl)-N-methylbutanamide (81)

Thionyl chloride (0.01 mL, 0.11 mmol) was added slowly to a solution of 4-(2-Fluoro-4-nitrophenyl)butanoic acid (82) (20 mg, 0.09 mmol) in DMF (3 mL) cooled at −5° C. The mixture was stirred for an additional 1 h at −5° C. Excess methylamine (freshly distilled from its 40% aqueous solution) was added to the reaction medium. The second mixture was stirred for an additional 1 h. Ethyl acetate (30 mL) was added to the mixture, which was washed with brine (2×30 mL). The organic layer was dried over $MgSO_4$, and concentrated to yield 4-(2-Fluoro-4-nitrophenyl)-N-methylbutanamide (81) (18 mg, 85%): 1H NMR δ 7.97 (dd, 1H, J=8.4, 2.2 Hz), 7.89 (dd, 1H, J=9.5, 2.2 Hz), 7.40 (dd, 1H, J=8.4, 7.3 Hz), 5.44 (br s, 1H), 2.81 (d, 3H, J=4.9 Hz) 2.79 (t, 2H, J=7.6 Hz) 2.22 (t, 2H, J=7.3 Hz) 1.96-2.04 (m, 2H).

4-(4-Amino-2-fluorophenyl)-N-methylbutanamide (80)

A solution of compound 4-(2-Fluoro-4-nitrophenyl)-N-methylbutanamide (81) (18 mg, 0.07 mmol), Fe (30 mg, 0.52 mmol) and AcOH (1 mL) in ethyl acetate (3 mL) was heated under reflux for 2 h. The reaction mixture was allowed to cool to 21° C. and then filtered. The organic layer was concentrated and the residue was purified with silica gel column chromatography (dichloromethane:acetone, 9:1) to give desired 4-(4-Amino-2-fluorophenyl)-N-methylbutanamide (80) (14 mg, 86%): 1H NMR δ 6.92 (dd, 1H, J=8.3, 8.2 Hz), 6.39 (dd, 1H, J=8.3, 2.0 Hz), 6.33 (dd, 1H, J=13.3, 2.0 Hz), 5.48 (br s, 1H), 3.69 (br s, 2H), 2.79 (d, 3H, J=4.8 Hz), 2.55 (t, 2H, J=7.4 Hz) 2.16 (t, 2H, J=7.5 Hz) 1.85-1.94 (m, 2H).

4-(4-(1-Cyanocyclobutylamino)-2-fluorophenyl)-N-methylbutanamide (79)

A mixture of 4-(4-Amino-2-fluorophenyl)-N-methylbutanamide (80) (8 mg, 0.04 mmol), cyclobutanone (5 mg, 0.08 mmol) and trimethylsilyl cyanide (TMSCN, 8 mg, 0.08 mmol) was heated to 80° C. and stirred for 15 h. To the medium was added ethyl acetate (2×20 mL) and then washed with water (2×20 mL). The organic layer was dried over $MgSO_4$ and concentrated and the residue was purified with silica gel column chromatography (dichloromethane:acetone, 9:1) to give 4-(4-(1-Cyanocyclobutylamino)-2-fluorophenyl)-N-methylbutanamide (79) (10 mg, 92%).

4-(4-(7-(4-Cyano-3-(trifluoromethyl)phenyl)-8-oxo-6-thioxo-5,7-diazaspiro[3.4]oct-an-5-yl)-2-fluorophenyl)-N-methylbutanamide (78) [ND-7]

A mixture of 4-(4-(1-Cyanocyclobutylamino)-2-fluorophenyl)-N-methylbutanamide (79) (7 mg, 0.02 mmol) and 4-isothiocyanato-2-trifluoromethylbenzonitrile (96) (12 mg, 0.05 mmol) in DMF (1 mL) was heated to 80° C. using microwave for 16 h. To this mixture was added methanol (3 mL) and aq. 1 N HCl (3 mL). The second mixture was refluxed for 1.5 h. After being cooled to room temperature, the reaction mixture was poured into cold water (30 mL) and extracted with ethyl acetate (30 mL). The organic layer was dried over $MgSO_4$, concentrated and the residue was purified with silica gel column chromatography (dichloromethane:acetone, 95:5) to give 4-(4-(7-(4-Cyano-3-(trifluoromethyl)phenyl)-8-oxo-6-thioxo-5,7-diazaspiro[3.4]oct-an-5-yl)-2-fluorophenyl)-N-methylbutanamide (78) [ND-7] (8 mg, 62%) as a pale yellowish solid: $^1$H NMR δ 7.98 (d, 1H, J=8.2 Hz) 7.97 (d, 1H, J=2.0 Hz) 7.84 (dd, 1H, J=8.2, 2.0 Hz), 7.43 (dd, 1H, J=8.0, 8.0 Hz), 7.06 (dd, 1H, J=8.0, 2.0 Hz), 7.02 (dd, 1H, J=9.7, 2.0 Hz), 2.83 (d, 3H, J=4.8 Hz) 2.78 (t, 2H, J=7.7 Hz) 2.63-2.71 (m, 2H), 2.51-2.62 (m, 2H), 2.27 (t, 2H, J=7.3 Hz) 2.18-2.27 (m, 1H), 2.00-2.09 (m, 2H), 1.66-1.76 (m, 1H); $^{13}$C NMR δ 179.9, 174.7, 172.8, 161.2 (d, J=247 Hz), 137.0, 135.2, 134.1 (d, J=9.6 Hz), 133.6 (q, J=33.7 Hz), 132.1, 131.9 (d, J=5.6 Hz), 130.8 (d, J=15.2 Hz), 127.1, 125.7 (d, J=3.9

Hz), 121.9 (q, J=272 Hz), 117.3 (d, J=22.3 Hz), 114.8, 110.0, 67.4, 35.8, 31.5, 28.3, 26.4, 25.6, 13.7.

4-(2-Fluoro-4-nitrophenyl)-N,N-dimethylbutanamide (77)

Thionyl chloride (0.01 mL, 0.11 mmol) was added slowly to a solution of 4-(2-Fluoro-4-nitrophenyl)butanoic acid (82) (18 mg, 0.08 mmol) in DMF (3 mL) cooled at −5° C. The mixture was stirred for an additional 1 h at −5° C. Excess dimethylamine (freshly distilled from its 40% aqueous solution) was added to the reaction medium. The second mixture was stirred for an additional 1 h. Ethyl acetate (30 mL) was added to the mixture, which was washed with brine (2×30 mL). The organic layer was dried over $MgSO_4$, and concentrated to yield 4-(2-Fluoro-4-nitrophenyl)-N,N-dimethylbutanamide (77) (18 mg, 87%): $^1H$ NMR δ 7.98 (dd, 1H, J=8.3, 2.1 Hz), 7.89 (dd, 1H, J=9.5, 2.1 Hz), 7.42 (dd, 1H, J=8.3, 7.4 Hz), 2.98 (s, 3H), 2.95 (s, 3H), 2.81 (t, 2H, J=7.6 Hz) 2.36 (t, 2H, J=7.2 Hz) 1.96-2.04 (m, 2H).

4-(4-Amino-2-fluorophenyl)-N,N-dimethylbutanamide (76)

A solution of compound 4-(2-Fluoro-4-nitrophenyl)-N,N-dimethylbutanamide (77) (15 mg, 0.06 mmol), Fe (20 mg, 0.37 mmol) and acetic acid (1 mL) in ethyl acetate (3 mL) was heated under reflux for 2 h. The reaction mixture was allowed to cool to 21° C. and then filtered. The organic layer was concentrated and the residue was purified with silica gel column chromatography (dichloromethane:acetone, 9:1) to give desired 4-(4-Amino-2-fluorophenyl)-N,N-dimethylbutanamide (76) (12 mg, 87%): $^1H$ NMR δ 6.95 (dd, 1H, J=8.3, 8.2 Hz), 6.40 (dd, 1H, J=8.3, 2.2 Hz), 6.35 (dd, 1H, J=11.6, 2.2 Hz), 3.66 (br s, 2H), 2.95 (s, 3H), 2.93 (s, 3H), 2.58 (t, 2H, J=7.4 Hz) 2.30 (t, 2H, J=7.6 Hz) 1.85-1.95 (m, 2H).

4-(4-(2-Cyanopropan-2-ylamino)-2-fluorophenyl)-N,N-dimethylbutanamide (75)

A mixture of 4-(4-Amino-2-fluorophenyl)-N,N-dimethylbutanamide (76) (10 mg, 0.05 mmol), cyclobutanone (6 mg, 0.09 mmol) and trimethylsilyl cyanide (TMSCN, 9 mg, 0.09 mmol) was heated to 80° C. and stirred for 15 h. To the medium was added ethyl acetate (2×20 mL) and then washed with water (2×20 mL). The organic layer was dried over $MgSO_4$ and concentrated and the residue was purified with silica gel column chromatography (dichloromethane:acetone, 9:1) to give 4-(4-(2-Cyanopropan-2-ylamino)-2-fluorophenyl)-N,N-dimethylbutanamide (75) (12 mg, 89%): $^1H$ NMR δ 7.04 (dd, 1H, J=8.0, 7.8 Hz), 6.36 (dd, 1H, J=8.0, 2.3 Hz), 6.32 (dd, 1H, J=11.6, 2.3 Hz), 4.08 (br s, 1H), 2.96 (s, 3H), 2.93 (s, 3H), 2.77-2.81 (m, 2H), 2.61 (t, 2H, J=7.4 Hz) 2.35-2.38 (m, 2H), 2.31 (t, 2H, J=7.6 Hz), 2.10-2.37 (m, 2H), 1.87-1.95 (m, 2H).

4-(4-(7-(4-Cyano-3-(trifluoromethyl)phenyl)-8-oxo-6-thioxo-5,7-diazaspiro[3.4]oct-an-5-yl)-2-fluorophenyl)-N,N-dimethylbutanamide (74) [ND-8]

A mixture of 4-(4-(2-Cyanopropan-2-ylamino)-2-fluorophenyl)-N,N-dimethylbutanamide (75) (7 mg, 0.02 mmol) and 4-isothiocyanato-2-trifluoromethylbenzonitrile (96) (12 mg, 0.05 mmol) in DMF (1 mL) was heated to 80° C. using microwave for 16 h. To this mixture was added methanol (3 mL) and aq. 1 N HCl (3 mL). The second mixture was refluxed for 1.5 h. After being cooled to room temperature, the reaction mixture was poured into cold water (30 mL) and extracted with ethyl acetate (30 mL). The organic layer was dried over $MgSO_4$, concentrated and the residue was purified with silica gel column chromatography (dichloromethane:acetone, 95:5) to give 4-(4-(7-(4-Cyano-3-(trifluoromethyl)phenyl)-8-oxo-6-thioxo-5,7-diazaspiro[3.4]oct-an-5-yl)-2-fluorophenyl)-N,N-dimethylbutanamide (74) [ND-8] (8 mg, 65%) as a pale yellowish solid: $^1H$ NMR δ 7.98 (d, 1H, J=8.2 Hz) 7.97 (d, 1H, J=2.1 Hz), 7.84 (dd, 1H, J=8.2, 2.1 Hz), 7.46 (dd, 1H, J=8.0, 8.0 Hz), 7.05 (dd, 1H, J=8.0, 2.2 Hz), 7.02 (dd, 1H, J=9.6, 2.2 Hz), 3.01 (s, 3H), 2.97 (s, 3H), 2.80 (t, 2H, J=7.8 Hz) 2.63-2.71 (m, 2H), 2.52-2.62 (m, 2H), 2.42 (t, 2H, J=7.4 Hz) 2.20-2.31 (m, 1H), 2.00-2.08 (m, 2H), 1.65-1.75 (m, 1H); $^{13}C$ NMR δ 179.9, 174.7 (2 C's), 161.3 (d, J=248 Hz), 137.0, 135.2, 134.1 (d, J=10.3 Hz), 133.6 (q, J=33.3 Hz), 132.1, 131.9 (d, J=5.7 Hz), 131.2 (d, J=16.2 Hz), 127.1, 125.7 (d, J=4.3 Hz), 121.9 (q, J=272 Hz), 117.2 (d, J=25.1 Hz), 114.8, 110.2, 67.5, 37.2, 35.5, 32.7, 31.6, 28.5, 25.2, 13.7.

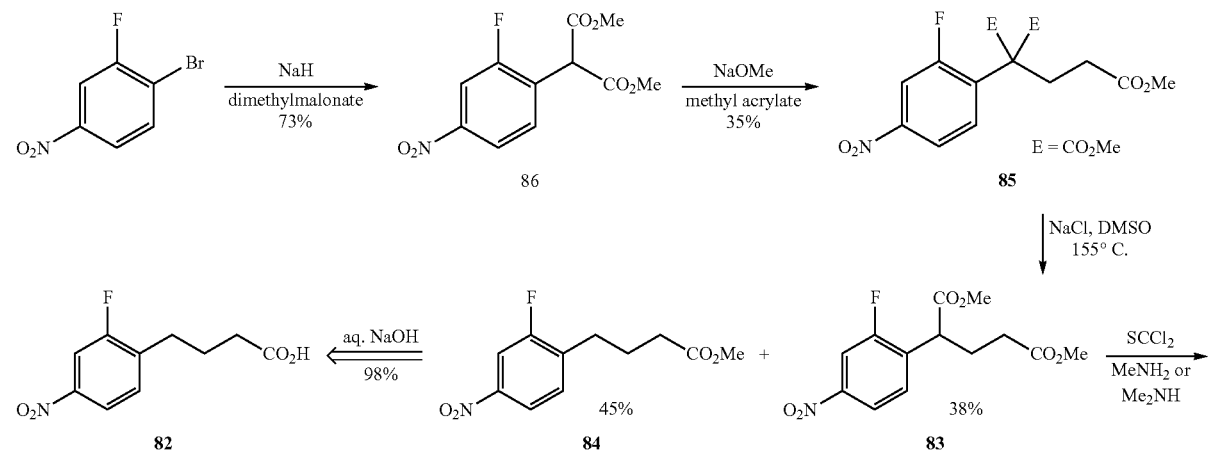

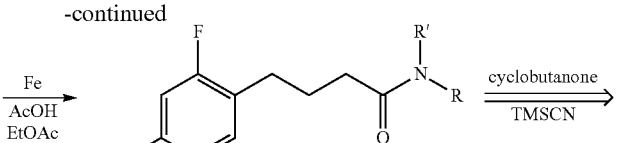

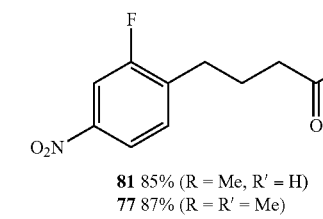

81 85% (R = Me, R' = H)
77 87% (R = R' = Me)

80 98% (R = Me, R' = H)
76 97% (R = R' = Me)

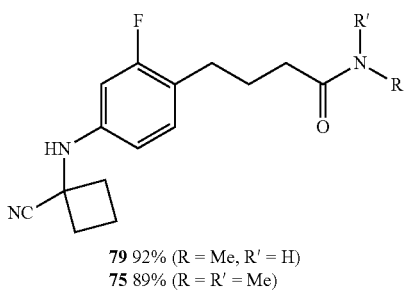

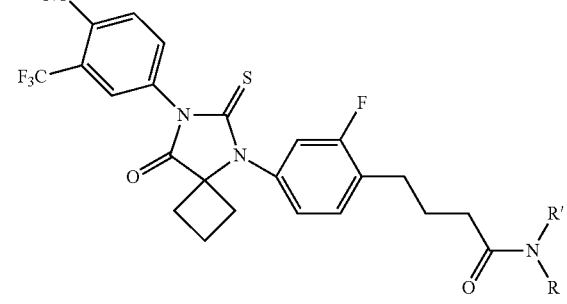

79 92% (R = Me, R' = H)
75 89% (R = R' = Me)

78 62% (R = Me, R' = H ND-7)
74 65% (R = R' = Me ND-8)

Synthesis of ND-9

Dimethyl 2-(2-cyanoethyl)-2-(2-fluoro-4-nitrophenyl)malonate (73)

To a solution of the nitro diester, Dimethyl 2-(2-fluoro-4-nitrophenyl)malonate (86) (0.4 g, 1.47 mmol) and acrylonitrile (0.11 mL, 1.62 mmol) in absolute methanol (5 mL) was added a catalytic amount of sodium methoxide at 21° C. under argon. The reaction mixture was stirred for 40 h at the same temperature and then diluted with dichloromethane (50 mL). The resulting mixture was washed with water, brine and dried. The residue obtained upon evaporation of the solvents was purified on a silica gel (hexane:ethyl acetate, 8:1) to give Dimethyl 2-(2-cyanoethyl)-2-(2-fluoro-4-nitrophenyl)malonate (73) (0.25 g, 52%): $^1$H NMR δ 8.07 (dd, 1H, J=8.7, 2.3 Hz), 7.99 (dd, 1H, J=10.9, 2.3 Hz), 7.47 (dd, 1H, J=8.7, 7.3 Hz), 3.85 (s, 6H), 2.65-2.70 (m, 2H), 2.47-2.51 (m, 2H).

4-(2-Fluoro-4-nitrophenyl)butanenitrile (72)

A solution of compound Dimethyl 2-(2-cyanoethyl)-2-(2-fluoro-4-nitrophenyl)malonate (73) (0.19 g, 0.59 mmol), sodium chloride (0.10 g, 1.76 mmol) and water (0.15 mL) in distilled dimethylsulfoxide (DMSO, 4 mL) was heated to 155° C. overnight. The reaction mixture was allowed to cool to 21° C. and then worked up by adding water and extracting with ethyl acetate (2×50 mL). The organic layer was dried over MgSO$_4$, concentrated and the residue was purified with silica gel column chromatography (hexane:ethyl acetate, 8:1) to give desired 4-(2-Fluoro-4-nitrophenyl)butanenitrile (72) (79 mg, 65%): $^1$H NMR δ 8.02 (dd, 1H, J=8.3, 2.2 Hz), 7.94 (dd, 1H, J=9.5, 2.2 Hz), 7.42 (dd, 1H, J=8.3, 7.4 Hz), 2.93 (t, 2H, J=7.7 Hz) 2.41 (t, 2H, J=7.0 Hz) 2.01-2.07 (m, 2H).

4-(4-Amino-2-fluorophenyl)butanenitrile (71)

A solution of compound 4-(2-Fluoro-4-nitrophenyl)butanenitrile (72) (47 mg, 0.23 mmol), Fe (78 mg, 1.40 mmol) and acetic acid (1 mL) in ethyl acetate (3 mL) was heated under reflux for 2 h. The reaction mixture was allowed to cool to 21° C. and then filtered. The organic layer was concentrated and the residue was purified with silica gel column chromatography (dichloromethane:acetone, 9:1) to give desired 4-(4-Amino-2-fluorophenyl)butanenitrile (71) (33 mg, 83%): $^1$H NMR δ 6.98-7.01 (m, 1H), 6.46-6.52 (m, 2H), 2.70 (t, 2H, J=7.6 Hz) 2.32 (t, 2H, J=7.2 Hz) 1.89-1.98 (m, 2H).

1-(4-(3-Cyanopropyl)-3-fluorobenzyl)cyclobutanecarbonitrile (70)

A mixture of 4-(4-Amino-2-fluorophenyl)butanenitrile (71) (30 mg, 0.17 mmol), cyclobutanone (24 mg, 0.34 mmol) and trimethylsilyl cyanide (TMSCN, 33 mg, 0.34 mmol) was heated to 80° C. and stirred for 15 h. To the medium was added ethyl acetate (2×20 mL) and then washed with water (2×20 mL). The organic layer was dried over MgSO$_4$ and concentrated and the residue was purified with silica gel column chromatography (dichloromethane:acetone, 9:1) to give 1-(4-(3-Cyanopropyl)-3-fluorobenzyl)cyclobutanecarbonitrile (70) (40 mg, 92%): $^1$H NMR δ 7.01 (dd, 1H, J=8.0, 7.5 Hz), 6.37 (dd, 1H, J=8.0, 2.4 Hz), 6.34 (dd, 1H, J=11.8, 2.4 Hz), 4.18 (br s, 1H), 2.76-2.81 (m, 2H), 2.70 (t, 2H, J=7.3 Hz), 2.33-2.39 (m, 2H), 2.33 (t, 2H, J=7.1 Hz) 2.12-2.30 (m, 2H), 1.90-1.95 (m, 2H).

4-(5-(4-(3-Cyanopropyl)-3-fluorophenyl)-8-oxo-6-thioxo-5,7-diazaspiro[3.4]octan-7-yl)-2-(trifluoromethyl)benzonitrile (69) [ND-9]

A mixture of 1-(4-(3-Cyanopropyl)-3-fluorobenzyl)cyclobutanecarbonitrile (70) (32 mg, 0.12 mmol) and 4-isothiocyanato-2-trifluoromethylbenzonitrile (96) (62 mg, 0.27 mmol) in DMF (1 mL) was heated to 80° C. using microwave for 16 h. To this mixture was added methanol (3 mL) and aq. 1 N HCl (3 mL). The second mixture was refluxed for 1.5 h. After being cooled to room temperature, the reaction mixture was poured into cold water (30 mL) and extracted with ethyl acetate (30 mL). The organic layer was dried over MgSO$_4$, concentrated and the residue was purified with silica gel column chromatography (dichloromethane:acetone, 95:5) to give 4-(5-(4-(3-Cyanopropyl)-3-fluorophenyl)-8-oxo-6-thioxo-5,7-diazaspiro[3.4]octan-7-yl)-2-(trifluoromethyl)

benzonitrile (69) [ND-9] (48 mg, 80%) as a pale yellowish solid: $^1$H NMR δ 7.98 (d, 1H, J=8.2 Hz) 7.97 (d, 1H, J=2.0 Hz) 7.84 (dd, 1H, J=8.2, 2.0 Hz), 7.44 (dd, 1H, J=8.0, 8.0 Hz), 7.10 (dd, 1H, J=8.0, 2.0 Hz), 7.07 (dd, 1H, J=10.2, 2.0 Hz), 2.92 (t, 2H, J=7.6 Hz) 2.64-2.71 (m, 2H), 2.51-2.61 (m, 2H), 2.45 (t, 2H, J=7.1 Hz), 2.20-2.31 (m, 1H), 2.03-2.11 (m, 2H), 1.64-1.75 (m, 1H); $^{13}$C NMR δ 179.9, 174.6, 161.3 (d, J=248 Hz), 137.0, 135.2, 134.9 (d, J=10.0 Hz), 133.6 (q, J=33.2 Hz), 132.2, 131.9 (d, J=5.8 Hz), 129.0 (d, J=15.7 Hz), 127.1, 126.0 (d, J=3.6 Hz), 121.9 (q, J=273 Hz), 119.1, 117.6 (d, J=23.4 Hz), 114.8, 110.1, 67.4, 31.6 (2 C's), 28.1, 25.4, 16.8, 13.7.

4:1) to give 4-(8-hydroxy-5-(4-(4-oxobutyl)phenyl)-6-thioxo-5,7-diazaspiro[3.4]octan-7-yl)-2-(trifluoromethyl) (66) (20 mg, 35%) and 4-(8-Oxo-5-(4-(4-oxobutyl)phenyl)-6-thioxo-5,7-diazaspiro[3.4]octan-7-yl)-2-(trifluoromethyl)benzonitrile (68) [ND-10] (23 mg, 40%): $^1$H NMR of (68) δ 9.81 (s, 1H), 7.98 (d, 1H, J=2.0 Hz) 7.97 (d, 1H, J=8.0 Hz) 7.86 (dd, 1H, J=8.2, 2.0 Hz), 7.40 (d, 1H, J=8.3 Hz) 7.24 (d, 1H, J=8.3 Hz) 2.76 (t, 2H, J=7.5 Hz) 2.63-2.67 (m, 2H), 2.57-2.63 (m, 2H), 2.55 (t, 2H, J=7.2 Hz) 2.13-2.31 (m, 1H), 2.01-2.07 (m, 2H), 1.57-1.77 (m, 1H).

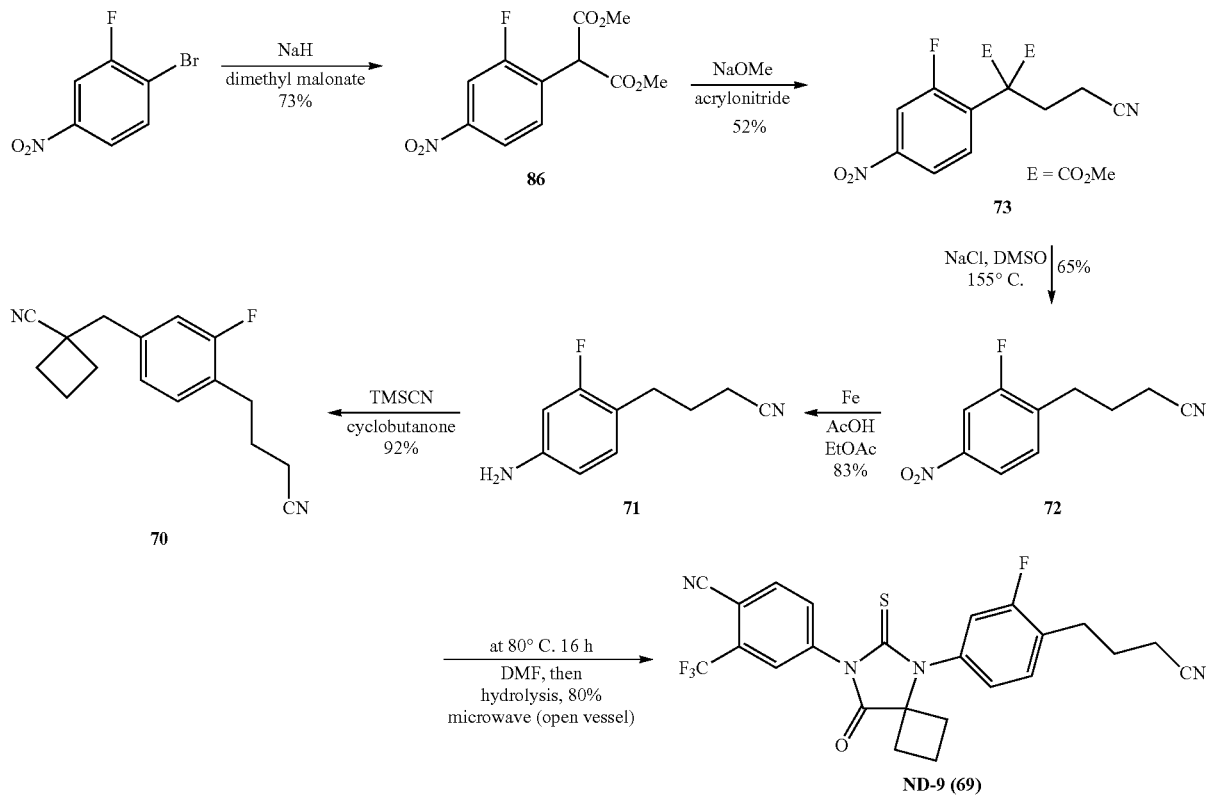

Synthesis of ND-11 and ND-10

4-(8-Oxo-5-(4-(4-oxobutyl)phenyl)-6-thioxo-5,7-diazaspiro[3.4]octan-7-yl)-2-(trifluoromethyl)benzonitrile (68) [ND-10]

To a stirred solution of 4-{4-[7-(4-cyano-3-trifluoromethylphenyl)-8-oxo-6-thioxo-5,7-diazaspiro[3.4]oct-5-yl]-phenyl}-butyric acid methyl ester (67) [ND-4] (61 mg, 0.12 mmol) in dichloromethane (5 mL), 1M diisobutylaluminum hydride (DIBAL) solution in hexane (0.16 mL, 0.16 mmol) was added at −78° C. After 30 min, the reaction mixture was quenched with saturated Rochelle's salt solution. The resulting mixture was stirred at 21° C. until both phases were clearly separated and the organic layer was clear. After extraction, the separated organic layer was dried over MgSO$_4$, filtered, and concentrated under vacuum. The crude mixture of (66) and (68) was purified by flash column chromatography (hexane:ethyl acetate, 4-(5-(4-(3-(4,5-Dihydro-1H-imidazol-2-yl)propyl)phenyl)-8-oxo-6-thioxo-5,7-diaza-spiro[3.4]octan-7-yl)-2-(trifluoromethyl)benzonitrile (65) [ND-11]

The mixture of 4-(8-Oxo-5-(4-(4-oxobutyl)phenyl)-6-thioxo-5,7-diazaspiro[3.4]octan-7-yl)-2-(trifluoromethyl)benzonitrile (68) [ND-10] (15 mg, 0.03 mmol) and ethylene diamine (2 μL, 0.04 mmol) in dry dichloromethane (3 mL) was stirred at 0° C. for 30 min under argon. N-Bromosuccinimide (NBS, 6 mg, 0.04 mmol) was added to the mixture and the resulting solution was stirred overnight at 21° C. Reaction was quenched by the addition of saturated NaHCO$_3$ solution. The mixture was extracted with dichloromethane. The organic layer was dried over MgSO$_4$, and evaporated in vacuo. The residue was purified by flash column chromatography (ethanol:ethyl acetate, 1:4) to give 4-(5-(4-(3-(4,5-Dihydro-1H-imidazol-2-yl)propyl)phenyl)-8-oxo-6-thioxo-5,7-diaza-spiro[3.4]octan-7-yl)-2-(trifluoromethyl)benzonitrile (65) [ND-11] (6 mg, 35%): $^1$H NMR δ 7.98 (d, 1H, J=1.9 Hz) 7.97 (d, 1H, J=8.3 Hz) 7.85 (dd, 1H, J=8.3, 1.9 Hz), 7.46 (d, 1H, J=8.2 Hz) 7.25 (d, 1H, J=8.2 Hz), 4.72 (br s, 1H), 3.67-3.80 (m, 4H), 2.85-3.05 (m, 2H), 2.57-2.70 (m, 2H), 2.43-2.57 (m, 4H), 2.15-2.30 (m, 1H), 1.63-1.80 (m, 3H).

An alternative route for synthesizing 2-(3-(4-Nitrophenyl) propyl)-4,5-dihydro-1H-imidazole (62) from methyl 4-(4-nitrophenyl)butanoate (63) was also used and is as follows.

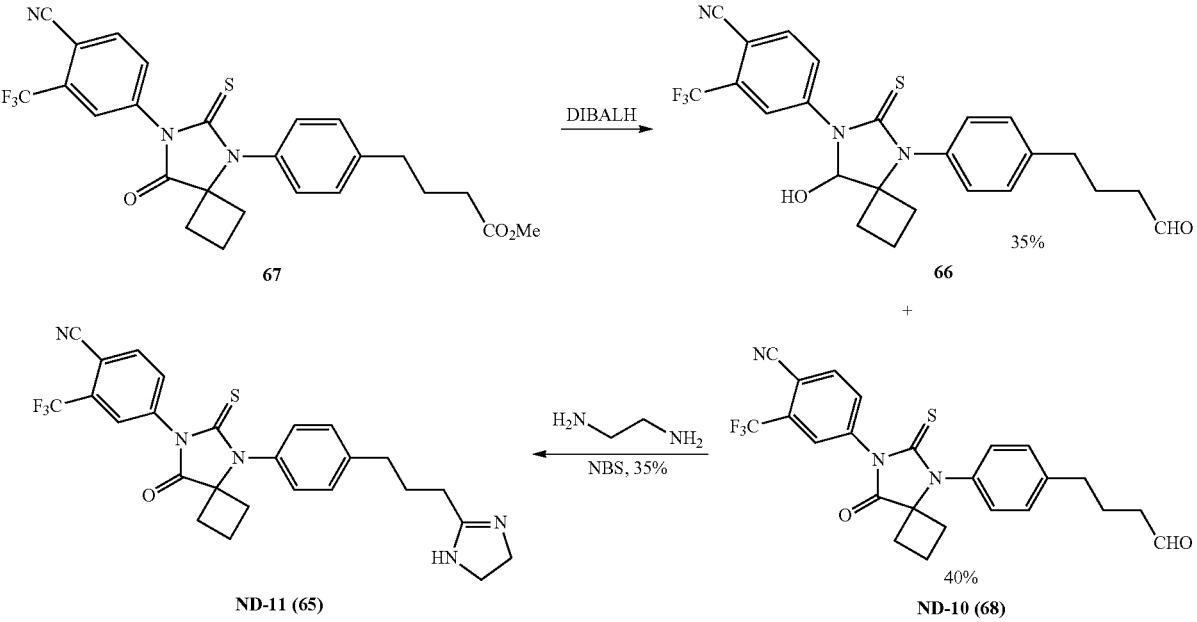

Synthesis of ND-12

4-(4-Nitrophenyl)butanal (64)

To a stirred solution of methyl 4-(4-nitrophenyl)butanoate (63) (0.45 g, 2.02 mmol) in dichloromethane (30 mL), 1M diisobutylaluminum hydride (DIBAL) solution in hexane (2.62 mL, 2.62 mmol) was added at −78° C. After 30 min, the reaction mixture was quenched with saturated Rochelle's salt solution. The resulting mixture was stirred at 21° C. until both phases were clearly separated and the organic layer was clear. After extraction, the separated organic layer was dried over $MgSO_4$, filtered, and concentrated under vacuum. The crude 4-(4-Nitrophenyl)butanal (64) was purified by flash column chromatography (hexane:ethyl acetate, 8:1) to give 4-(4-Nitrophenyl)butanal (64) (0.28 g, 72%): $^1$H NMR δ 9.79 (s, 1H), 8.16 (d, 2H, J=8.7 Hz) 7.34 (d, 2H, J=8.7 Hz) 2.77 (t, 2H, J=7.7 Hz) 2.51 (t, 2H, J=7.1 Hz), 1.95-2.04 (m, 2H).

2-(3-(4-Nitrophenyl)propyl)-4,5-dihydro-1H-imidazole (62)

The mixture of 4-(4-Nitrophenyl)butanal (64) (0.28 g, 1.45 mmol) and ethylene diamine (0.1 mL, 1.59 mmol) in dry dichloromethane (10 mL) was stirred at 0° C. for 30 min under argon. NBS (0.26 g, 1.59 mmol) was added to the mixture and the resulting solution was stirred overnight at 21° C. Reaction was quenched by the addition of saturated $NaHCO_3$ solution. The mixture was extracted with dichloromethane. The organic layer was dried over $MgSO_4$, and evaporated in vacuo. The residue was purified by flash column chromatography (ethanol:ethyl acetate:triethylamine, 1:1:0.2) to give 2-(3-(4-Nitrophenyl)propyl)-4,5-dihydro-1H-imidazole (62) (0.26 g, 76%): $^1$H NMR δ 8.14 (d, 2H, J=8.7 Hz) 7.35 (d, 2H, J=8.7 Hz) 3.59 (s, 4H), 2.79 (t, 2H, J=7.7 Hz) 2.26 (t, 2H, J=7.4 Hz) 1.96-2.05 (m, 2H).

Ethylenediamine (0.1 mL, 1.59 mmol) was added dropwise to a stirred solution of trimethylaluminum (1.59 mmol) in 2 mL of toluene, so that the temperature did not exceed 10° C. At the end of methane evolution the ester (63) (0.22 g, 1.00 mmol) was gradually added at room temperature. The reaction mixture was refluxed for 3 h. After cooling, the solution was treated dropwise with 1 mL of water, diluted with 3 mL of methanol and 3 mL of methylene chloride, and refluxed on a steam bath for 15 min. After filtration over $MgSO_4$ and solvent evaporation the residue was purified by flash column chromatography (ethanol:ethyl acetate:triethylamine, 1:1:0.2) to give 2-(3-(4-Nitrophenyl)propyl)-4,5-dihydro-1H-imidazole (62) (0.10 g, 45%): $^1$H NMR δ 8.14 (d, 2H, J=8.7 Hz) 7.35 (d, 2H, J=8.7 Hz) 3.59 (s, 4H), 2.79 (t, 2H, J=7.7 Hz) 2.26 (t, 2H, J=7.4 Hz) 1.96-2.05 (m, 2H).

tert-Butyl 2-(3-(4-nitrophenyl)propyl)-1H-imidazole-1-carboxylate (61)

To a solution of dichloromethane (5 mL) and dimethylsulfoxide (0.06 mL, 0.79 mmol) was added oxalyl chloride (0.07 mL, 0.79 mmol) at −78° C. under an argon atmosphere. After stirring for 20 min, a solution of 2-(3-(4-Nitrophenyl)propyl)-4,5-dihydro-1H-imidazole (62) (74 mg, 0.32 mmol) in dichloromethane was added to the reaction mixture. After stirring for 50 min, triethylamine (0.22 mL, 1.59 mmol) was added and then the reaction mixture was warmed to room temperature. After stirring for 50 min, aqueous ammonia solution (10 mL) was added and the resulting mixture was extracted with chloroform (20 mL). The combined organic layer was washed with brine, dried, filtered and concentrated under reduced pressure. The residue was purified by flash column chromatography (dichloromethane:methanol, 10:1) to give the corresponding imidazole (61 mg, 83%). To a solution of the imidazole (50 mg, 0.22 mmol) in dichloromethane (5 mL) was added triethylamine (0.04 mL, 0.26 mmol) and tert-butoxycarbonyl anhydride (Boc₂O, 57 mg, 0.26 mmol). The reaction mixture was stirred at 21° C. overnight. The reaction mixture was extracted with dichloromethane (20 mL). The organic layer was washed with brine, dried, filtered and concentrated under reduced pressure. The residue was purified by flash column chromatography (dichloromethane:methanol, 20:1) to give tert-Butyl 2-(3-(4-nitrophenyl)propyl)-1H-imidazole-1-carboxylate (61) (72 mg, quant.): ¹H NMR δ 8.14 (d, 2H, J=8.7 Hz) 7.37 (d, 2H, J=8.7 Hz) 7.30 (d, 1H, J=1.7 Hz) 6.86 (d, 1H, J=1.7 Hz), 3.05 (t, 2H, J=7.6 Hz) 2.85 (t, 2H, J=7.7 Hz) 2.11-2.19 (m, 2H), 1.60 (s, 9H).

tert-Butyl 2-(3-(4-(1-cyanocyclobutylamino)phenyl)propyl)-1H-imidazole-1-carboxylate (60)

To a solution of tert-Butyl 2-(3-(4-nitrophenyl)propyl)-1H-imidazole-1-carboxylate (61) (72 mg, 0.22 mmol) in ethyl acetate (5 mL) was introduced hydrogen gas in the presence of a catalytic amount of Pd/C. After completion of the reaction, the reaction mixture was filtered, concentrated and then purified by flash column chromatography (dichloromethane:methanol, 10:1) to give the corresponding amine (59 mg, 90%): ¹H NMR δ 7.30 (d, 1H, J=1.7 Hz) 7.00 (d, 2H, J=8.3 Hz) 6.85 (d, 1H, J=1.7 Hz) 6.62 (d, 2H, J=8.3 Hz), 3.54 (br s, 2H), 3.01 (t, 2H, J=7.8 Hz) 2.62 (t, 2H, J=7.7 Hz) 2.01-2.08 (m, 2H), 1.65 (s, 9H). A mixture of the amine (55 mg, 0.18 mmol), cyclobutanone (26 mg, 0.36 mmol) and trimethylsilyl cyanide (TMSCN, 36 mg, 0.36 mmol) was heated to 80° C. and stirred for 15 h. To the medium was added ethyl acetate (2×20 mL) and then washed with water (2×20 mL). The organic layer was dried over MgSO₄ and concentrated and the residue was purified with silica gel column chromatography (dichloromethane:acetone, 9:1) to give tert-Butyl 2-(3-(4-(1-cyanocyclobutylamino)phenyl)propyl)-1H-imidazole-1-carboxylate (60) (57 mg, 82%): ¹H NMR δ 7.30 (d, 1H, J=1.7 Hz) 7.09 (d, 2H, J=8.4 Hz) 6.85 (d, 1H, J=1.7 Hz) 6.58 (d, 2H, J=8.4 Hz), 3.92 (br s, 1H), 3.01 (t, 2H, J=7.7 Hz) 2.74-2.80 (m, 2H), 2.64 (t, 2H, J=7.6 Hz) 2.29-2.42 (m, 2H), 2.10-2.27 (m, 2H), 2.01-2.09 (m, 2H), 1.60 (s, 9H).

4-(5-(4-(3-(1H-Imidazol-2-yl)propyl)phenyl)-8-oxo-6-thioxo-5,7-diazaspiro[3.4]octan-7-yl)-2-(trifluoromethyl)benzonitrile (59) [ND-12]

A mixture of tert-Butyl 2-(3-(4-(1-cyanocyclobutylamino)phenyl)propyl)-1H-imidazole-1-carboxylate (60) (22 mg, 0.06 mmol) and 4-isothiocyanato-2-trifluoromethylbenzonitrile (96) (26 mg, 0.12 mmol) in DMF (1 mL) was heated to 80° C. using microwave for 16 h. To this mixture was added methanol (3 mL) and aq. 1 N HCl (3 mL). The second mixture was refluxed for 1.5 h. After being cooled to room temperature, the reaction mixture was poured into cold water (30 mL), treated with saturated NaHCO₃ solution and extracted with ethyl acetate (50 mL). The organic layer was dried over MgSO₄, concentrated and the residue was purified with silica gel column chromatography (dichloromethane:acetone, 9:1) to give 4-(5-(4-(3-(1H-Imidazol-2-yl)propyl)phenyl)-8-oxo-6-thioxo-5,7-diazaspiro[3.4]octan-7-yl)-2-(trifluoromethyl)benzonitrile (59) [ND-12] (29 mg, 52%) as a pale yellowish solid: ¹H NMR δ 8.65 (br s, 1H), 7.97 (d, 1H, J=2.0 Hz) 7.96 (d, 1H, J=8.4 Hz) 7.84 (dd, 1H, J=8.4, 2.0 Hz), 7.34 (d, 2H, J=8.2 Hz) 7.19 (d, 2H, J=8.2 Hz) 3.00 (t, 2H, J=7.5 Hz) 2.73 (t, 2H, J=7.7 Hz), 2.47-2.77 (m, 4H), 2.13-2.25 (m, 3H), 1.51-1.71 (m, 1H).

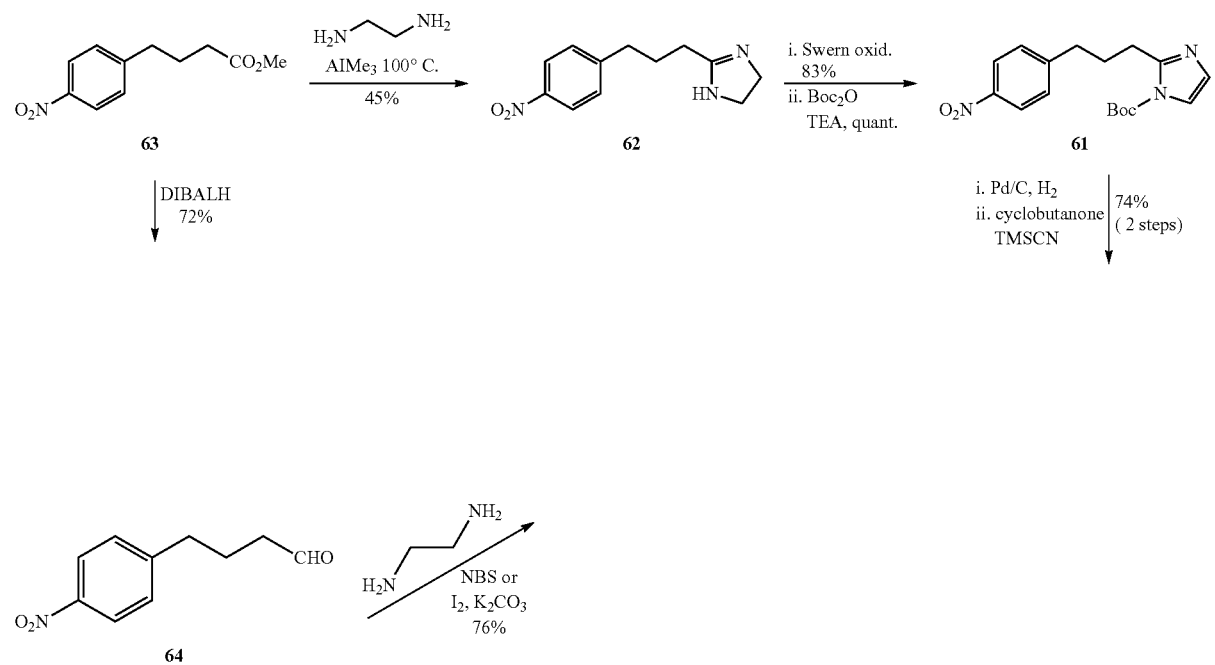

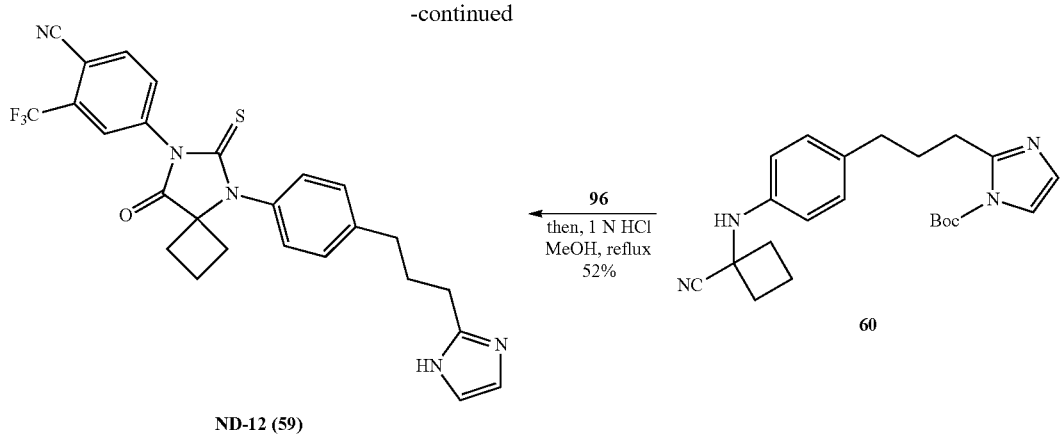

ND-12 (59)

One skilled in the art could modify and/or combine the syntheses described herein to make other diarylhydantoin compounds.

Synthesis of ND-13

4-(4-(7-(4-Cyano-3-(trifluoromethyl)phenyl)-8-oxo-6-thioxo-5,7-diazaspiro[3.4]oct-an-5-yl)-2-fluorophenyl)-2,2-dimethyl-N-methylbutanamide (113)

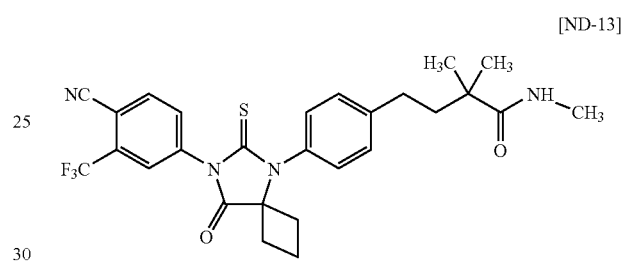

Another compound envisioned is 4-(4-(7-(4-Cyano-3-(trifluoromethyl)phenyl)-8-oxo-6-thioxo-5,7-diazaspiro[3.4]oct-an-5-yl)-2-fluorophenyl)-2,2-dimethyl-N-methylbutanamide (113) [ND-13].

An example of a synthetic route for making 4-(4-(7-(4-Cyano-3-(trifluoromethyl)phenyl)-8-oxo-6-thioxo-5,7-diazaspiro[3.4]oct-an-5-yl)-2-fluorophenyl)-2,2-dimethyl-N-methylbutanamide (113) [ND-13] is below.

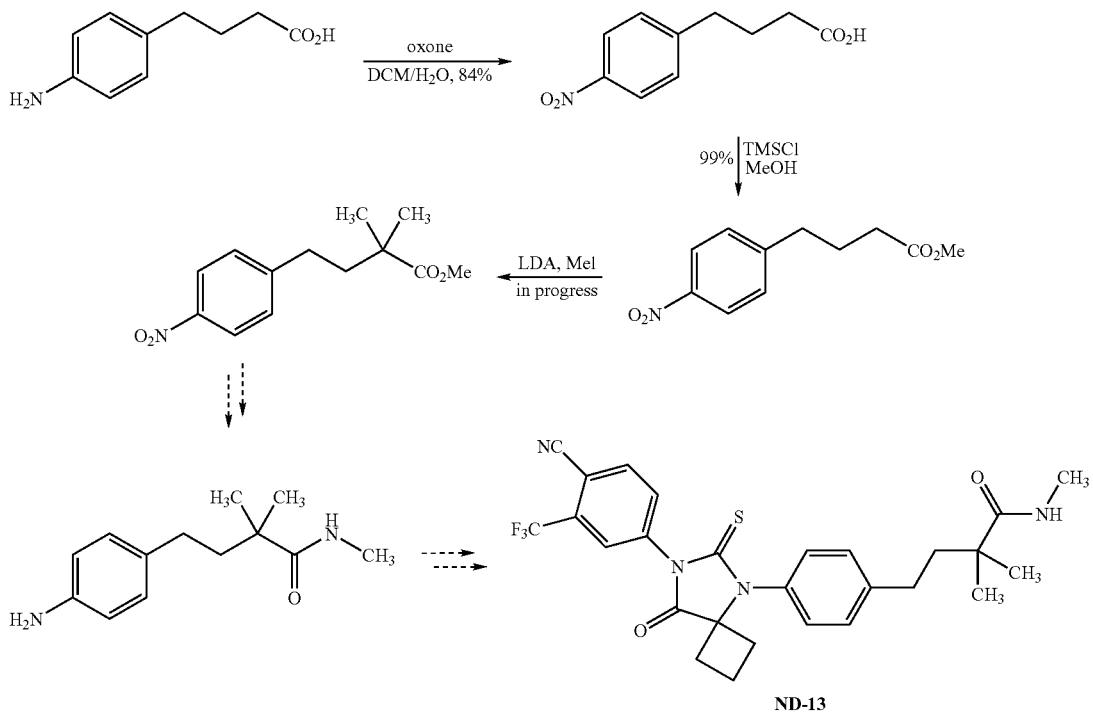

Alternatively, 4-(4-(7-(4-Cyano-3-(trifluoromethyl)phenyl)-8-oxo-6-thioxo-5,7-diazaspiro[3.4]oct-an-5-yl)-2-fluorophenyl)-2,2-dimethyl-N-methylbutanamide (113) [ND-13] can be synthesized in a manner similar as to that for synthesizing (92) [ND-2]. A mixture of 4-Isothiocyanato-2-trifluoromethylbenzonitrile (96) and 4-(4-(1-cyanocyclobutylamino)phenyl)-N,2,2-trimethylbutanamide (111) in solvent, for example, in DMF, is heated under microwave irradiation at 80° C. for 6 h.

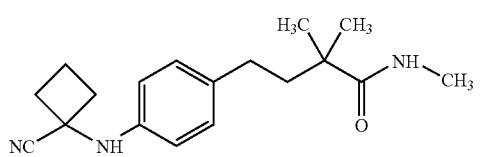

111

To this mixture is added alcohol, e.g., methanol, and acid, e.g., aqueous hydrochloric acid. The second mixture is refluxed for 1.5 h. After being cooled to room temperature, the reaction mixture is poured into cold water and extracted, for example, with ethyl acetate. The organic layer is dried, e.g., dried over MgSO$_4$, concentrated, and the residue is purified, for example, by silica gel column chromatography using hexane:ethyl acetate (2:1), to give 4-(4-(7-(4-Cyano-3-(trifluoromethyl)phenyl)-8-oxo-6-thioxo-5,7-diazaspiro[3.4]oct-an-5-yl)-2-fluorophenyl)-2,2-dimethyl-N-methylbutanamide (113) [ND-13].

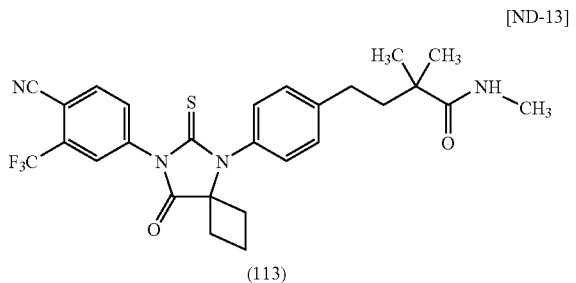

[ND-13]

(113)

Inventive compounds also include those with the following formulas.

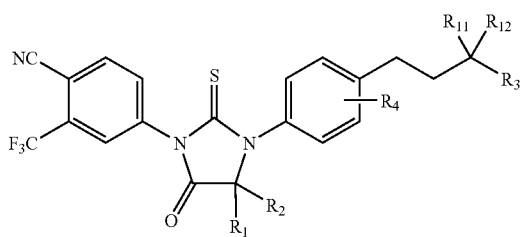

$R_1$ and $R_2$ together can comprise eight or fewer carbon atoms and can be alkyl, substituted alkyl, or, together with the carbon to which they are linked, a cycloalkyl or substituted cycloalkyl group. $R_3$ can be hydrogen, cyano, formyl,

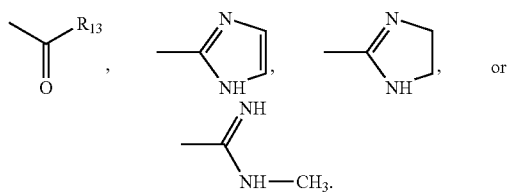

$R_4$ can be hydrogen, F, Cl, Br, and I. $R_{11}$ and $R_{12}$ can be the same or different and can be hydrogen or methyl. $R_{13}$ can be hydrogen or —$NR_{14}R_{15}$. $R_{14}$ and $R_{15}$ can be the same or different and can be hydrogen or methyl.

Pharmacological Examination of the Compounds

Compounds for which synthetic routes are described above can be evaluated through screening on hormone refractory prostate cancer cells for antagonistic and agonistic activities against AR utilizing screening procedures similar to those in PCT applications bearing numbers US04/42221, US05/05529, and US06/11417 and U.S. application Ser. No. 11/433,829, which are hereby incorporated by reference.

In Vitro Biological Assay

Effect of Compounds on AR by a Reporter Assay

For example, the compounds can be subjected to tests using an artificial androgen receptor (AR) response reporter system in a hormone refractory prostate cancer cell line. The prostate cancer LNCaP cells are engineered to stably express about 5-fold higher level of AR than endogenous level. The exogenous AR has similar properties to endogenous AR in that both are stabilized by a synthetic androgen R1881. The AR-over expressed cells are also engineered to stably incorporate an AR response reporter and the reporter activity of these cells shows features of hormone refractory prostate cancer. It responds to low concentration of a synthetic androgen R1881, is inhibited only by high concentrations of bicalutamide, and displays agonistic activity with bicalutamide. Bicalutamide inhibits AR response reporter and does not have agonistic activity in hormone sensitive prostate cancer cells.

The antagonistic activity of the compounds for which the synthesis is described above can be examined in the presence of 100 pM of R1881. Engineered LNCaP cells (LNCaP-AR, also abbreviated LN-AR) are maintained in Iscove's medium containing 10% fetal bovine serum (FBS). Two days prior to drug treatment, the cells are grown in Iscove's medium containing 10% charcoal-stripped FBS (CS-FBS) to deprive of androgens. The cells are split and grown in Iscove's medium containing 10% CS-FBS with 100 pM of R1881 and increasing concentrations of test compounds. After two days of incubation, reporter activities are assayed. Bicalutamide is used as a control substance.

One previously unrecognized property of AR overexpression in hormone refractory prostate cancer is its ability to switch antagonists to agonists. Therefore, only those compounds with minimal or no agonistic activities are qualified to be anti-androgens for this disease. To determine agonistic activities of different compounds, the stimulating activities on androgen receptor (AR) using the AR response reporter as the measure in the LN-AR system in the absence of R1881 can be examined. Bicalutamide can activate AR in hormone refractory prostate cancer. RU59063 and other anti-androgenic compounds listed as examples in U.S. Pat. No. 5,705,654 can activate AR in hormone refractory prostate cancer.

To examine the specificity of AR inhibitors, compounds can be tested in LNCaP cells with an over expression of glucocorticoid receptor (GR), the closest member of AR in the nuclear receptor family. These cells also carry a GR response reporter and the reporter activity can be induced by dexamethasone, a GR agonist, and the induction can be blocked by RU486, a GR inhibitor.

Effect of Compounds on AR by Measuring Secreted Levels of Prostate Specific Antigen (PSA)

PSA levels are indicators of androgen receptor (AR) activities in prostate cancer. To examine if the compounds affect AR function in a physiological environment, secreted levels of endogenous PSA induced by R1881 in the AR-overexpressed LNCaP cells (LNCaP-AR, also abbreviated LN-AR) can be determined. The LNCaP-AR cells are a line of lymph node carcinoma of prostate cells transduced with a plasmid that makes express androgen receptors. LNCaP-AR cells are maintained in Iscove's medium containing 10% FBS. Two days prior to drug treatment, the cells are grown in Iscove's medium containing 10% CS-FBS to deprive of androgens. The cells are split and grown in Iscove's medium containing 10% CS-FBS with appropriate concentrations of R1881 and the test compounds. After four days incubation, secreted PSA levels are assayed using PSA ELISA kits (American Qualex, San Clemente, Calif.)

The secreted PSA level of LNCaP-AR cells are strongly induced by 25 pM of R1881. In contrast, PSA is not induced in the parental LNCaP cells until concentration of R1881 reached 100 pM. Thus, the AR in hormone refractory prostate cancer is hyper-sensitive to androgens. A dose-dependent inhibition on AR activity is carried out to determine the IC50s of different compounds in inhibiting PSA expression.

Agonistic activities of selective compounds on AR in hormone refractory prostate cancer can be examined using secreted PSA as the surrogate marker. To do this, androgen-starved AR over expressed LNCaP cells are incubated with increasing concentrations of the compounds for which a synthesis is described above in the absence of R1881 and secreted PSA in the culture medium are measured 4 days later.

RU59063 and other antiandrogenic compounds listed as examples in U.S. Pat. No. 5,705,654 can stimulate PSA expression in hormone refractory prostate cancer.

Effect of Compounds on AR Mitochondrial Activity by MTS Assay

LNCaP-AR cells can be maintained in Iscove's medium containing 10% FBS. The compounds are examined for their effect on growth of hormone refractory prostate cancer cells. Overexpressed LNCaP cells are used because these cells behave as hormone refractory prostate cancer cells in vitro and in vivo. Mitochondria activity by MTS assay is measured, a surrogate for growth. LNCaP cells with overexpressed AR (LN-AR) are maintained in Iscove's medium containing 10% FBS. Two days prior to drug treatment, the cells are grown in Iscove's medium containing 10% CS-FBS to deprive of androgens. The cells are then split and grown in Iscove's medium containing 10% CS-FBS with appropriate concentrations of R1881 and increasing concentrations of the test compounds. After four days incubation, cell growth is monitored by MTS (Promega, Madison, Wis.).

Consistent with the reporter assay and PSA assay, growth of the AR-overexpressed LNCaP is stimulated by 25 microM of R1881, but the parental cells are not stimulated until R1881 concentration reaches 100 microM. The inhibitory effect of compounds on growth of hormone refractory prostate cancer in the presence of 100 pM of R1881 is measured. Bicalutamide does not inhibit hormone refractory prostate cancer.

To examine whether growth inhibition in the MTS assay occurs by targeting AR, compounds can be tested in DU-145 cells, a prostate cancer cell line that lacks AR expression. The compounds can be tested for their ability to inhibit cells other than AR-expressed prostate cancer cells, such as MCF7 and SkBr3, two commonly used breast cancer cells, or 3T3, a normal mouse fibroblast cell line.

Based on the observations with various assays, the compounds can be ranked in order of their activity.

Inhibitory Effect on Hormone Refractory Prostate Cancer Xenograft Tumors

The in vivo effects of compounds on hormone refractory prostate cancer can be examined. The effect of compounds on xenograft tumors established from AR-overexpressed LNCaP cells can be examined. The engineered cells in Matrigel (Collaborative Biomedical) are injected subcutaneously into the flanks of the castrated male SCID mice. Tumor size is measured weekly in three dimensions using calipers. After xenograft tumors become established (for example, with a tumor size of at least 40 mm$^3$), mice with tumors are randomized and treated with different doses of compounds orally once daily. Bicalutamide does not inhibit growth of hormone refractory prostate cancer, the same as vehicle.

Compounds can also be tested in another xenograft model of hormone refractory prostate cancer, hormone refractory LAPC4. This model is established from passaging of hormone sensitive prostate cancer in castrated mice, which mimics the clinical progression of prostate cancer. Bicalutamide does not inhibit growth and PSA expression in hormone refractory LAPC4 xenograft model, the same as vehicle.

Inhibitory Effect on Growth of Hormone Sensitive Prostate Cancer Cells

To determine if compounds inhibit hormone sensitive prostate cancer cells, the effect of the compounds on growth of LNCaP cells can be examined by measuring MTS of mitochondria activities. Bicalutamide mildly inhibits hormone sensitive LNCaP cells in a dose-dependent manner.

In Vivo Biological Assay

Animal experiments are performed in compliance with the guidelines of the Animal Research Committee of the University of California at Los Angeles. Animals are bought from Taconic and maintained in a laminar flow tower in a defined flora colony. LNCaP-AR and LNCaP-vector cells are maintained in RPMI medium supplemented with 10% FBS. $10^6$ cells in 100 μl of 1:1 Matrigel to RPMI medium are injected subcutaneously into the flanks of intact or castrated male SCID mice. Tumor size is measured weekly in three dimensions (length×width×depth) using calipers. Mice are randomized to treatment groups when tumor size reaches approximately 100 mm$^3$. Drugs are given orally every day at 10 mg/kg and 50 mg/kg. To obtain pharmacodynamic readout, the animals are imaged via an optical CCD camera, 3 hours after last dose of the treatment. An ROI is drawn over the tumor for luciferase activity measurement in photon/second.

The pharmacokinetics of bicalutamide and compounds being tested is evaluated in vivo using 8 week-old FVB mice which are purchased from Charles River Laboratories. Mice are divided into groups of three for each time points. Two mice are not treated with drug and two other mice are treated with vehicle solution. Each group is treated with 10 mg per kilogram of body weight.

The drug is dissolved in a mixture 1:5:14 of DMSO:PEG400:$H_2O$. (Vehicle solution) and is administered into mice through the tail vein. The animals are warmed under a heat lamp for approximately 20 minutes prior to treatment to dilate their tail vein. Each mouse is placed into a mouse restrainer (Fisher Sci. Cat# 01-288-32A) and is injected with 200 μl of drug in vehicle solution into the dilated tail vein. After drug administration, the animals are euthanized via $CO_2$ inhalation at different timepoints: 5 nm, 30 nm, 2 h, 6 h, 16 h. Animals are immediately bled after exposure to $CO_2$ via cardiac puncture (1 ml BD syringe+27G ⅝ needle). For oral dosage, the drug is dissolved in a mixture 50:10:1:989 of DMSO:Carboxymethylcellulose:Tween80:$H_2O$ before oral administration via a feeding syringe.

The serum samples are analyzed to determine the drug's concentration by the HPLC which (Waters 600 pump, Waters 600 controller and Waters 2487 detector) is equipped with an Alltima C18 column (3μ, 150 mm×4.6 mm). For example, the compounds being tested can be detected at 254 nm wave length and bicalutamide can be detected at 270 nm wave length.

The samples for HPLC analysis are prepared according to the following procedure:

Blood cells are separated from serum by centrifugation.

To 400 μl of serum are added 80 μl of a 10 μM solution of an internal standard and 520 μl of acetonitrile. Precipitation is watched for.

The mixture is vortexed for 3 minutes and then placed under ultrasound for 30 minutes.

The solid particles are filtered off or are separated by centrifugation.

The filtrate is dried under an argon flow to dryness. The sample is reconstituted to 80 μl with acetonitrile before analyzing by HPLC to determine the drug concentration.

Standard curve of drug is used to improve accuracy.

The steady state concentration (Css) of a compound can be determined and compared with that of bicalutamide.

Ranking of Compounds

To rank the compounds, the following data can be considered: in vitro assays (AR response reporter system in LNCaP cell line, PSA level measurement, MTS mitochondrial assay) and in vivo experiments (tumor size measured directly or by emission induced by luciferase reporter gene, pharmacokinetic assays based on blood plasma levels). Characteristics considered in establishing a ranking can include androgen receptor (AR) antagonism activity, lack of AR agonism in hormone refractory cells, prevention of tumor growth, tumor shrinkage, and pharmacokinetic behavior, with a longer residence time in blood being advantageous.

Compounds that are highly ranked can be advantageous for use as AR antagonists, and as therapeutic agents for hormone refractory prostate cancer. They may be useful to treat other AR related diseases or conditions such as benign prostate hyperplasia, hair loss, and acne. Highly ranked compounds may also be useful as modulators of other nuclear receptors, such as glucocorticoid receptor, estrogen receptor, and peroxisome proliferator-activated receptor, and as therapeutic agents for diseases in which nuclear receptors play a role, such as breast cancer, ovarian cancer, diabetes, cardiac diseases, and metabolism related diseases. They may be useful in assays, e.g., as standards, or as intermediates or prodrugs.

The compounds presented in this application can be superior to bicalutamide in treating prostate cancer.

Pharmaceutical Compositions and Administration

The compounds of the invention are useful as pharmaceutical compositions prepared with a therapeutically effective amount of a compound of the invention, as defined herein, and a pharmaceutically acceptable carrier or diluent.

The diarylhydantoin compounds of the invention can be formulated as pharmaceutical compositions and administered to a subject in need of treatment, for example a mammal, such as a human patient, in a variety of forms adapted to the chosen route of administration, for example, orally, nasally, intraperitoneally, or parenterally, by intravenous, intramuscular, topical or subcutaneous routes, or by injection into tissue.

Thus, diarylhydantoin compounds of the invention may be systemically administered, e.g., orally, in combination with a pharmaceutically acceptable vehicle such as an inert diluent or an assimilable edible carrier, or by inhalation or insufflation. They may be enclosed in hard or soft shell gelatin capsules, may be compressed into tablets, or may be incorporated directly with the food of the patient's diet. For oral therapeutic administration, the diarylhydantoin compounds may be combined with one or more excipients and used in the form of ingestible tablets, buccal tablets, troches, capsules, elixirs, suspensions, syrups, wafers, and the like. The diarylhydantoin compounds may be combined with a fine inert powdered carrier and inhaled by the subject or insufflated. Such compositions and preparations should contain at least 0.1% diarylhydantoin compounds. The percentage of the compositions and preparations may, of course, be varied and may conveniently be between about 2% to about 60% of the weight of a given unit dosage form. The amount of diarylhydantoin compounds in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the diarylhydantoin compounds may be incorporated into sustained-release preparations and devices. For example, the diarylhydantoin compounds may be incorporated into time release capsules, time release tablets, and time release pills.

The diarylhydantoin compounds may also be administered intravenously or intraperitoneally by infusion or injection.

Solutions of the diarylhydantoin compounds can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the diarylhydantoin compounds which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the diarylhydantoin compounds in the required amount in the appropriate solvent with various of the other ingredients enumerated above, as required, followed by filter sterilization. In the case of sterile powders for the preparation of sterile injectable solutions, the preferred methods of preparation are vacuum drying and freeze drying techniques, which yield a powder of the active ingredient plus any additional desired ingredient present in the previously sterile-filtered solutions.

For topical administration, the diarylhydantoin compounds may be applied in pure form. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Other solid carriers include nontoxic polymeric nanoparticles or microparticles. Useful liquid carriers include water, alcohols or glycols or water/alcohol/glycol blends, in which the diarylhydantoin compounds can be dissolved or dispersed at effective levels, optionally with the aid of nontoxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the diarylhydantoin compounds to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508), all of which are hereby incorporated by reference.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949, which is hereby incorporated by reference.

For example, the concentration of the diarylhydantoin compounds in a liquid composition, such as a lotion, can be from about 0.1-25% by weight, or from about 0.5-10% by weight. The concentration in a semi-solid or solid composition such as a gel or a powder can be about 0.1-5% by weight, or about 0.5-2.5% by weight.

The amount of the diarylhydantoin compounds required for use in treatment will vary not only with the particular salt selected but also with the route of administration, the nature of the condition being treated and the age and condition of the patient and will be ultimately at the discretion of the attendant physician or clinician.

Effective dosages and routes of administration of agents of the invention are conventional. The exact amount (effective dose) of the agent will vary from subject to subject, depending on, for example, the species, age, weight and general or clinical condition of the subject, the severity or mechanism of any disorder being treated, the particular agent or vehicle used, the method and scheduling of administration, and the like. A therapeutically effective dose can be determined empirically, by conventional procedures known to those of skill in the art. See, e.g., *The Pharmacological Basis of Therapeutics*, Goodman and Gilman, eds., Macmillan Publishing Co., New York. For example, an effective dose can be estimated initially either in cell culture assays or in suitable animal models. The animal model may also be used to determine the appropriate concentration ranges and routes of administration. Such information can then be used to determine useful doses and routes for administration in humans. A therapeutic dose can also be selected by analogy to dosages for comparable therapeutic agents.

The particular mode of administration and the dosage regimen will be selected by the attending clinician, taking into account the particulars of the case (e.g., the subject, the disease, the disease state involved, and whether the treatment is prophylactic). Treatment may involve daily or multi-daily doses of compound(s) over a period of a few days to months, or even years.

In general, however, a suitable dose will be in the range of from about 0.001 to about 100 mg/kg, e.g., from about 0.01 to about 100 mg/kg of body weight per day, such as above about 0.1 mg per kilogram, or in a range of from about 1 to about 10 mg per kilogram body weight of the recipient per day. For example, a suitable dose may be about 0.1 mg/kg, 1 mg/kg, 10 mg/kg, or 50 mg/kg of body weight per day.

The diarylhydantoin compounds are conveniently administered in unit dosage form; for example, containing 0.05 to 10000 mg, 0.5 to 10000 mg, 5 to 1000 mg, or about 100 mg of active ingredient per unit dosage form.

The diarylhydantoin compounds can be administered to achieve peak plasma concentrations of, for example, from about 0.5 to about 75 µM, about 1 to 50 µM, about 2 to about 30 µM, or about 5 to about 25 µM. Exemplary desirable plasma concentrations include at least or no more than 0.01, 0.025, 0.05, 0.1, 0.25, 0.5, 1, 5, 10, 25, 50, 75, 100 or 200 µM. For example, plasma levels may be from about 1 to 100 micromolar or from about 10 to about 25 micromolar. This may be achieved, for example, by the intravenous injection of a 0.05 to 5% solution of the diarylhydantoin compounds, optionally in saline, or orally administered as a bolus containing about 1-100 mg of the diarylhydantoin compounds. Desirable blood levels may be maintained by continuous infusion to provide about 0.00005-5 mg per kg body weight per hour, for example at least or no more than 0.00005, 0.0005, 0.005, 0.05, 0.5, or 5 mg/kg/hr. Alternatively, such levels can be obtained by intermittent infusions containing about 0.0002-20 mg per kg body weight, for example, at least or no more than 0.0002, 0.002, 0.02, 0.2, 2, 20, or 50 mg of the diarylhydantoin compounds per kg of body weight.

The diarylhydantoin compounds may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator.

A number of the above-identified compounds exhibit little or no agonistic activities with respect to hormone refractory prostate cancer cells. Because these compounds are strong androgen receptor (AR) inhibitors, they can be used not only in treating prostate cancer, but also in treating other AR related diseases or conditions such as benign prostate hyperplasia, hair loss, and acne. Because AR belongs to the family of nuclear receptors, these compounds may serve as scaffolds for drug synthesis targeting other nuclear receptors, such as estrogen receptor and peroxisome proliferator-activated receptor. Therefore, they may be further developed for other diseases such as breast cancer, ovarian cancer, diabetes, cardiac diseases, and metabolism related diseases, in which nuclear receptors play a role.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

The invention claimed is:

1. A compound of formula

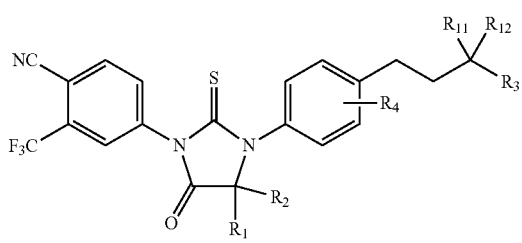

wherein $R_1$ and $R_2$ together comprise eight or fewer carbon atoms and are alkyl, or are substituted alkyl, or, together with the carbon to which they are linked, form a cycloalkyl or substituted cycloalkyl group, wherein $R_4$ is selected from the group consisting of hydrogen, F, Cl, Br, and I, wherein $R_{11}$ and $R_{12}$ are independently selected from the group consisting of hydrogen and methyl, wherein $R_3$ is selected from the group consisting of

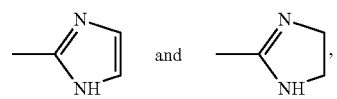

and pharmaceutical salts thereof.

2. A compound of formula

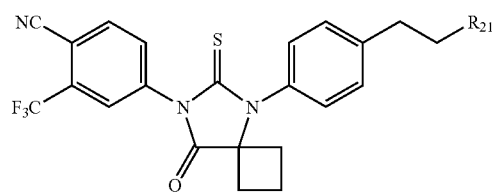

wherein $R_{21}$ is selected from the group consisting of

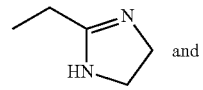

[ND-11]

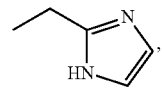

[ND-12]

and pharmaceutical salts thereof.

3. A compound of formula

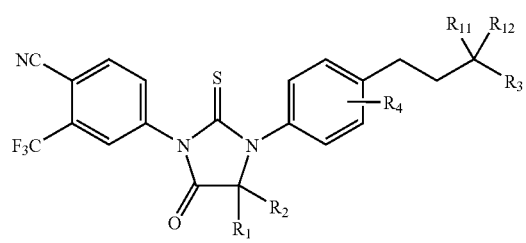

wherein $R_1$ and $R_2$ together comprise eight or fewer carbon atoms and are alkyl, or are substituted alkyl, or, together with the carbon to which they are linked, form a cycloalkyl or substituted cycloalkyl group, wherein $R_4$ is selected from the group consisting of hydrogen, F, Cl, Br, and I, wherein $R_{11}$ and $R_{12}$ are independently selected from the group consisting of hydrogen and methyl, wherein $R_3$ is selected from the group consisting of formyl,

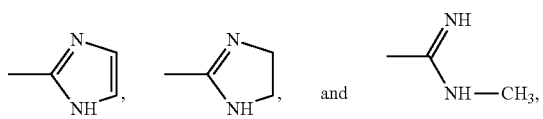

provided that when $R_4$, $R_{11}$, and $R_{12}$ are all hydrogen and when $R_1$ and $R_2$ together with the carbon to which they are linked are cyclobutyl, then $R_3$ is not formyl, and pharmaceutical salts thereof.

4. The compound of claim 3, of the formula

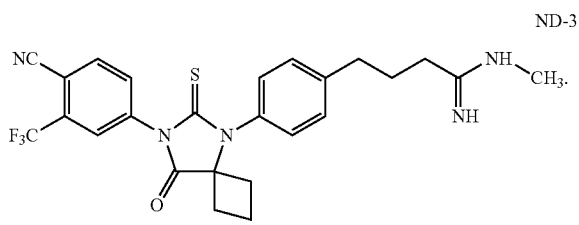 [SMILES: CNC(=N)CCCc1ccc(N2C(=S)N(c3ccc(C#N)c(C(F)(F)F)c3)C(=O)C23CCC3)cc1]

ND-3.

5. The compound of claim 3, of the formula

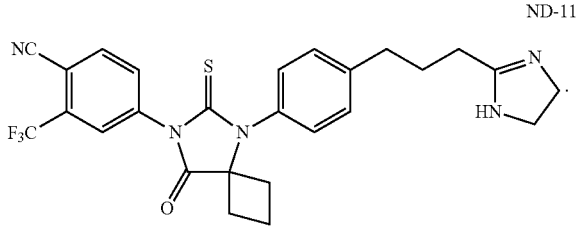 [SMILES: N#Cc1ccc(N2C(=O)C3(CCC3)N(c3ccc(CCCc4ncc[nH]4)cc3)C2=S)cc1C(F)(F)F ; "."]

ND-11.

6. The compound of claim 3, of the formula

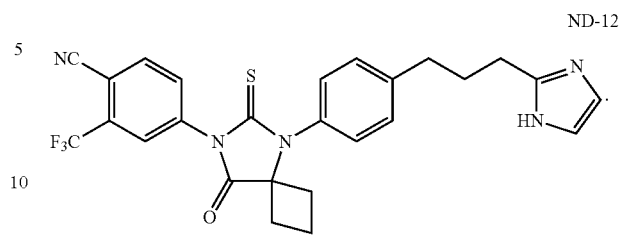

ND-12.

7. A pharmaceutical composition comprising a therapeutically effective amount of a compound according to claim 1 or a pharmaceutically acceptable salt thereof, and a pharmaceutically acceptable carrier or diluent.

8. The pharmaceutical composition of claim 7, having a form selected from the group consisting of a solution, dispersion, suspension, powder, capsule, tablet, pill, time release capsule, time release tablet, and time release pill.

9. A pharmaceutical composition comprising a therapeutically effective amount of a compound according to claim 2 or a pharmaceutically acceptable salt thereof, and a pharmaceutically acceptable carrier or diluent.

10. The pharmaceutical composition of claim 9, having a form selected from the group consisting of a solution, dispersion, suspension, powder, capsule, tablet, pill, time release capsule, time release tablet, and time release pill.

11. A pharmaceutical composition comprising a therapeutically effective amount of a compound according to claim 3 or a pharmaceutically acceptable salt thereof, and a pharmaceutically acceptable carrier or diluent.

12. The pharmaceutical composition of claim 11, having a form selected from the group consisting of a solution, dispersion, suspension, powder, capsule, tablet, pill, time release capsule, time release tablet, and time release pill.

\* \* \* \* \*